(12) United States Patent
Yuen et al.

(10) Patent No.: US 9,039,614 B2
(45) Date of Patent: *May 26, 2015

(54) METHODS, SYSTEMS AND DEVICES FOR MEASURING FINGERTIP HEART RATE

(71) Applicant: Fitbit, Inc., San Francisco, CA (US)

(72) Inventors: Shelten Yuen, Berkeley, CA (US); Subramaniam Venkatraman, San Francisco, CA (US); Eric Van Albert, San Francisco, CA (US); James Park, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/302,360

(22) Filed: Jun. 11, 2014

(65) Prior Publication Data

US 2014/0296658 A1  Oct. 2, 2014

Related U.S. Application Data

(63) Continuation of application No. 14/156,381, filed on Jan. 15, 2014, now Pat. No. 8,827,906.

(60) Provisional application No. 61/924,547, filed on Jan. 7, 2014, provisional application No. 61/752,826, filed on Jan. 15, 2013, provisional application No. 61/830,600, filed on Jun. 3, 2013.

(51) Int. Cl.
*A61B 5/00* (2006.01)
*A61B 5/11* (2006.01)
*A61B 5/024* (2006.01)

(52) U.S. Cl.
CPC ............... *A61B 5/721* (2013.01); *A61B 5/1118* (2013.01); *A61B 5/1112* (2013.01);

(Continued)

(58) Field of Classification Search
None
See application file for complete search history.

(56) References Cited

U.S. PATENT DOCUMENTS 2,284,849 A  8/1941  Anderson et al.
2,717,736 A  9/1955  Schlesinger (Continued)

FOREIGN PATENT DOCUMENTS

JP  11347021  12/1999
WO  WO 2006055125 A1  5/2006

(Continued)

OTHER PUBLICATIONS

"A Hybrid Discriminative/Generative Approach for Modeling Human Activities", Lester, et al., Proc. of the Int'l Joint Conf. Artificial Intelligence, 2005, pp. 766-772.

(Continued)

*Primary Examiner* — William Thomson
*Assistant Examiner* — Bobby Soriano
(74) *Attorney, Agent, or Firm* — Martine Penilla Group, LLP

(57) ABSTRACT

A system and method of tracking activity includes a motion sensor, a light source and a light detector. The light detector is configured to capture an amount of the light that is reflected back to the light detector, at least a first portion of the light reflected back to the light detector is reflected from a blood vessel disposed under a skin of a user when the user places the skin over the heart rate monitor location on the housing. A processor is in communication with the motion sensor and the light detector and can process the reflected light to identify heart beats of the user and produce an indication of a heart rate. The indication of the heart rate can be displayed on the display screen as an option, in addition to the metrics that quantify the motion data.

22 Claims, 11 Drawing Sheets

(52) U.S. Cl.
CPC .......... *A61B 5/6826* (2013.01); *A61B 5/02433* (2013.01); *A61B 5/6885* (2013.01); *A61B 5/742* (2013.01); *A61B 5/0022* (2013.01); *A61B 5/681* (2013.01); *A61B 2503/10* (2013.01)

(56) References Cited

U.S. PATENT DOCUMENTS

| | | | |
|---|---|---|---|
| 2,827,309 A | | 3/1958 | Fred |
| 2,883,255 A | | 4/1959 | Anderson |
| 3,163,856 A | | 12/1964 | Kirby |
| 3,250,270 A | | 5/1966 | Walter |
| 3,522,383 A | | 7/1970 | Chang |
| 3,918,658 A | | 11/1975 | Beller |
| 4,192,000 A | | 3/1980 | Lipsey |
| 4,244,020 A | | 1/1981 | Ratcliff |
| 4,281,663 A | | 8/1981 | Pringle |
| 4,284,849 A | | 8/1981 | Anderson et al. |
| 4,312,358 A | | 1/1982 | Barney |
| 4,367,752 A | | 1/1983 | Jimenez et al. |
| 4,390,922 A | | 6/1983 | Pelliccia |
| 4,407,295 A | | 10/1983 | Steuer et al. |
| 4,425,921 A * | | 1/1984 | Fujisaki et al. ............... 600/503 |
| 4,575,804 A | | 3/1986 | Ratcliff |
| 4,578,769 A | | 3/1986 | Frederick |
| 4,617,525 A | | 10/1986 | Lloyd |
| 4,887,249 A | | 12/1989 | Thinesen |
| 4,977,509 A | | 12/1990 | Pitchford et al. |
| 5,058,427 A | | 10/1991 | Brandt |
| 5,224,059 A | | 6/1993 | Nitta et al. |
| 5,295,085 A | | 3/1994 | Hoffacker |
| 5,323,650 A | | 6/1994 | Fullen et al. |
| 5,365,930 A * | | 11/1994 | Takashima et al. ............ 600/485 |
| 5,446,705 A | | 8/1995 | Haas et al. |
| 5,456,648 A | | 10/1995 | Edinburg et al. |
| 5,583,776 A | | 12/1996 | Levi et al. |
| 5,645,509 A | | 7/1997 | Brewer et al. |
| 5,671,162 A | | 9/1997 | Werbin |
| 5,704,350 A | | 1/1998 | Williams, III |
| 5,724,265 A | | 3/1998 | Hutchings |
| 5,890,128 A | | 3/1999 | Diaz et al. |
| 5,891,042 A | | 4/1999 | Sham et al. |
| 5,894,454 A * | | 4/1999 | Kondo ............................ 368/11 |
| 5,899,963 A | | 5/1999 | Hutchings |
| 5,941,828 A * | | 8/1999 | Archibald et al. ............ 600/494 |
| 5,947,868 A | | 9/1999 | Dugan |
| 5,955,667 A | | 9/1999 | Fyfe |
| 5,976,083 A | | 11/1999 | Richardson et al. |
| 6,018,705 A | | 1/2000 | Gaudet et al. |
| 6,077,193 A | | 6/2000 | Buhler et al. |
| 6,085,248 A | | 7/2000 | Sambamurthy et al. |
| 6,129,686 A | | 10/2000 | Friedman |
| 6,145,389 A | | 11/2000 | Ebeling et al. |
| 6,183,425 B1 | | 2/2001 | Whalen et al. |
| 6,213,872 B1 | | 4/2001 | Harada et al. |
| 6,241,684 B1 | | 6/2001 | Amano et al. |
| 6,287,262 B1 | | 9/2001 | Amano et al. |
| 6,301,964 B1 | | 10/2001 | Fyfe et al. |
| 6,302,789 B2 | | 10/2001 | Harada et al. |
| 6,305,221 B1 | | 10/2001 | Hutchings |
| 6,309,360 B1 | | 10/2001 | Mault |
| 6,469,639 B2 | | 10/2002 | Tanenhaus et al. |
| 6,478,736 B1 | | 11/2002 | Mault |
| 6,513,381 B2 | | 2/2003 | Fyfe et al. |
| 6,513,532 B2 | | 2/2003 | Mault et al. |
| 6,527,711 B1 | | 3/2003 | Stivoric et al. |
| 6,529,827 B1 | | 3/2003 | Beason et al. |
| 6,558,335 B1 * | | 5/2003 | Thede ........................... 600/503 |
| 6,561,951 B2 | | 5/2003 | Cannon et al. |
| 6,571,200 B1 | | 5/2003 | Mault |
| 6,585,622 B1 | | 7/2003 | Shum et al. |
| 6,607,493 B2 | | 8/2003 | Song |
| 6,620,078 B2 | | 9/2003 | Pfeffer |
| 6,678,629 B2 | | 1/2004 | Tsuji |
| 6,699,188 B2 | | 3/2004 | Wessel |
| 6,761,064 B2 | | 7/2004 | Tsuji |
| 6,790,178 B1 | | 9/2004 | Mault et al. |
| 6,808,473 B2 | | 10/2004 | Hisano et al. |
| 6,811,516 B1 | | 11/2004 | Dugan |
| 6,813,582 B2 | | 11/2004 | Levi et al. |
| 6,813,931 B2 | | 11/2004 | Yadav et al. |
| 6,856,938 B2 | | 2/2005 | Kurtz |
| 6,862,575 B1 | | 3/2005 | Anttila et al. |
| 7,041,032 B1 | | 5/2006 | Calvano |
| 7,062,225 B2 | | 6/2006 | White |
| 7,133,690 B2 | | 11/2006 | Ranta-Aho et al. |
| 7,162,368 B2 | | 1/2007 | Levi et al. |
| 7,171,331 B2 | | 1/2007 | Vock et al. |
| 7,200,517 B2 | | 4/2007 | Darley et al. |
| 7,246,033 B1 | | 7/2007 | Kudo |
| 7,261,690 B2 | | 8/2007 | Teller et al. |
| 7,272,982 B2 | | 9/2007 | Neuhauser et al. |
| 7,373,820 B1 | | 5/2008 | James |
| 7,443,292 B2 | | 10/2008 | Jensen et al. |
| 7,457,724 B2 | | 11/2008 | Vock et al. |
| 7,467,060 B2 | | 12/2008 | Kulach et al. |
| 7,502,643 B2 * | | 3/2009 | Farringdon et al. ........... 600/509 |
| 7,505,865 B2 | | 3/2009 | Ohkubo et al. |
| 7,559,877 B2 | | 7/2009 | Parks et al. |
| 7,653,508 B1 | | 1/2010 | Kahn et al. |
| 7,690,556 B1 | | 4/2010 | Kahn et al. |
| 7,713,173 B2 | | 5/2010 | Shin et al. |
| 7,762,952 B2 * | | 7/2010 | Lee et al. ....................... 600/300 |
| 7,771,320 B2 | | 8/2010 | Riley et al. |
| 7,774,156 B2 | | 8/2010 | Niva et al. |
| 7,789,802 B2 | | 9/2010 | Lee et al. |
| 7,881,902 B1 | | 2/2011 | Kahn et al. |
| 7,927,253 B2 | | 4/2011 | Vincent et al. |
| 7,983,876 B2 | | 7/2011 | Vock et al. |
| 8,028,443 B2 | | 10/2011 | Case, Jr. |
| 8,055,469 B2 | | 11/2011 | Kulach et al. |
| 8,099,318 B2 | | 1/2012 | Moukas et al. |
| 8,132,037 B2 | | 3/2012 | Fehr et al. |
| 8,177,260 B2 | | 5/2012 | Tropper et al. |
| 8,180,591 B2 | | 5/2012 | Yuen et al. |
| 8,180,592 B2 | | 5/2012 | Yuen et al. |
| 8,270,297 B2 | | 9/2012 | Akasaka et al. |
| 8,311,769 B2 | | 11/2012 | Yuen et al. |
| 8,311,770 B2 | | 11/2012 | Yuen et al. |
| 8,386,008 B2 | | 2/2013 | Yuen et al. |
| 8,437,980 B2 | | 5/2013 | Yuen et al. |
| 8,462,591 B1 | | 6/2013 | Marhaben |
| 8,463,576 B2 | | 6/2013 | Yuen et al. |
| 8,463,577 B2 | | 6/2013 | Yuen et al. |
| 8,533,620 B2 | | 9/2013 | Hoffman et al. |
| 8,543,185 B2 | | 9/2013 | Yuen et al. |
| 8,543,351 B2 | | 9/2013 | Yuen et al. |
| 8,548,770 B2 | | 10/2013 | Yuen et al. |
| 8,562,489 B2 | | 10/2013 | Burton et al. |
| 8,583,402 B2 | | 11/2013 | Yuen et al. |
| 8,597,093 B2 | | 12/2013 | Engelberg et al. |
| 8,634,796 B2 | | 1/2014 | Johnson |
| 8,670,953 B2 | | 3/2014 | Yuen et al. |
| 8,690,578 B1 | | 4/2014 | Nusbaum et al. |
| 8,738,321 B2 | | 5/2014 | Yuen et al. |
| 8,738,323 B2 | | 5/2014 | Yuen et al. |
| 8,744,803 B2 | | 6/2014 | Park et al. |
| 8,762,101 B2 | | 6/2014 | Yuen et al. |
| 8,847,988 B2 * | | 9/2014 | Geisner et al. ................ 345/633 |
| 2001/0049470 A1 | | 12/2001 | Mault et al. |
| 2001/0055242 A1 | | 12/2001 | Deshmukh et al. |
| 2002/0013717 A1 | | 1/2002 | Ando et al. |
| 2002/0019585 A1 * | | 2/2002 | Dickinson ..................... 600/300 |
| 2002/0077219 A1 | | 6/2002 | Cohen et al. |
| 2002/0082144 A1 | | 6/2002 | Pfeffer |
| 2002/0087264 A1 | | 7/2002 | Hills et al. |
| 2002/0109600 A1 | | 8/2002 | Mault et al. |
| 2002/0178060 A1 | | 11/2002 | Sheehan |
| 2002/0198776 A1 | | 12/2002 | Nara et al. |
| 2003/0018523 A1 | | 1/2003 | Rappaport et al. |
| 2003/0050537 A1 | | 3/2003 | Wessel |
| 2003/0065561 A1 | | 4/2003 | Brown et al. |
| 2003/0131059 A1 | | 7/2003 | Brown et al. |
| 2004/0054497 A1 | | 3/2004 | Kurtz |
| 2004/0061324 A1 | | 4/2004 | Howard |

(56) References Cited

U.S. PATENT DOCUMENTS

| | | |
|---|---|---|
| 2004/0117963 A1 | 6/2004 | Schneider |
| 2004/0152957 A1 | 8/2004 | Stivoric et al. |
| 2004/0239497 A1 | 12/2004 | Schwartzman et al. |
| 2004/0249299 A1 | 12/2004 | Cobb |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0163056 A1 | 7/2005 | Ranta-Aho et al. |
| 2005/0171410 A1 | 8/2005 | Hjelt et al. |
| 2005/0228244 A1* | 10/2005 | Banet .................... 600/301 |
| 2005/0228692 A1 | 10/2005 | Hodgdon |
| 2005/0234742 A1 | 10/2005 | Hodgdon |
| 2005/0248718 A1 | 11/2005 | Howell et al. |
| 2005/0272564 A1 | 12/2005 | Pyles et al. |
| 2006/0020177 A1 | 1/2006 | Seo et al. |
| 2006/0025282 A1 | 2/2006 | Redmann |
| 2006/0047208 A1 | 3/2006 | Yoon |
| 2006/0047447 A1 | 3/2006 | Brady et al. |
| 2006/0064276 A1 | 3/2006 | Ren et al. |
| 2006/0069619 A1 | 3/2006 | Walker et al. |
| 2006/0089542 A1 | 4/2006 | Sands |
| 2006/0111944 A1 | 5/2006 | Sirmans, Jr. |
| 2006/0129436 A1 | 6/2006 | Short |
| 2006/0143645 A1 | 6/2006 | Vock et al. |
| 2006/0217231 A1 | 9/2006 | Parks et al. |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2007/0050715 A1 | 3/2007 | Behar |
| 2007/0051369 A1 | 3/2007 | Choi et al. |
| 2007/0071643 A1* | 3/2007 | Hall et al. .................. 422/62 |
| 2007/0123391 A1 | 5/2007 | Shin et al. |
| 2007/0136093 A1 | 6/2007 | Rankin et al. |
| 2007/0146116 A1 | 6/2007 | Kimbrell |
| 2007/0155277 A1 | 7/2007 | Amitai et al. |
| 2007/0159926 A1 | 7/2007 | Prstojevich et al. |
| 2007/0179356 A1 | 8/2007 | Wessel |
| 2007/0194066 A1 | 8/2007 | Ishihara et al. |
| 2007/0197920 A1* | 8/2007 | Adams ....................... 600/483 |
| 2007/0208544 A1 | 9/2007 | Kulach et al. |
| 2007/0276271 A1 | 11/2007 | Chan |
| 2008/0032864 A1* | 2/2008 | Hakki ........................ 482/8 |
| 2008/0084823 A1 | 4/2008 | Akasaka et al. |
| 2008/0093838 A1 | 4/2008 | Tropper et al. |
| 2008/0125288 A1 | 5/2008 | Case |
| 2008/0140163 A1 | 6/2008 | Keacher et al. |
| 2008/0140338 A1 | 6/2008 | No et al. |
| 2008/0155077 A1 | 6/2008 | James |
| 2009/0018797 A1 | 1/2009 | Kasama et al. |
| 2009/0043531 A1 | 2/2009 | Kahn et al. |
| 2009/0048044 A1 | 2/2009 | Oleson et al. |
| 2009/0054737 A1 | 2/2009 | Magar et al. |
| 2009/0063193 A1 | 3/2009 | Barton et al. |
| 2009/0098821 A1 | 4/2009 | Shinya |
| 2009/0171788 A1 | 7/2009 | Tropper et al. |
| 2009/0262088 A1 | 10/2009 | Moll-Carrillo et al. |
| 2009/0264713 A1* | 10/2009 | Van Loenen et al. ......... 600/301 |
| 2009/0271147 A1 | 10/2009 | Sugai |
| 2009/0307517 A1 | 12/2009 | Fehr et al. |
| 2010/0059561 A1 | 3/2010 | Ellis et al. |
| 2010/0069203 A1 | 3/2010 | Kawaguchi et al. |
| 2010/0185064 A1* | 7/2010 | Bandic et al. ................. 600/306 |
| 2010/0205541 A1* | 8/2010 | Rapaport et al. ............... 715/753 |
| 2010/0217099 A1* | 8/2010 | LeBoeuf et al. ............... 600/301 |
| 2011/0003665 A1 | 1/2011 | Burton et al. |
| 2011/0009051 A1 | 1/2011 | Khedouri et al. |
| 2011/0022349 A1 | 1/2011 | Stirling et al. |
| 2011/0080349 A1 | 4/2011 | Holbein et al. |
| 2011/0106449 A1 | 5/2011 | Chowdhary et al. |
| 2011/0131005 A1 | 6/2011 | Ueshima et al. |
| 2011/0193704 A1 | 8/2011 | Harper et al. |
| 2011/0197157 A1 | 8/2011 | Hoffman et al. |
| 2011/0224508 A1* | 9/2011 | Moon .......................... 600/301 |
| 2011/0230729 A1* | 9/2011 | Shirasaki et al. ............. 600/301 |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0119911 A1 | 5/2012 | Jeon et al. |
| 2012/0183939 A1 | 7/2012 | Aragones et al. |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0265480 A1 | 10/2012 | Oshima |
| 2012/0274508 A1 | 11/2012 | Brown et al. |
| 2012/0330109 A1 | 12/2012 | Tran |
| 2013/0006718 A1 | 1/2013 | Nielsen et al. |
| 2013/0041590 A1 | 2/2013 | Burich et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0095459 A1 | 4/2013 | Tran |
| 2013/0096843 A1 | 4/2013 | Yuen et al. |
| 2013/0106684 A1 | 5/2013 | Weast et al. |
| 2013/0151196 A1 | 6/2013 | Yuen et al. |
| 2013/0158369 A1 | 6/2013 | Yuen et al. |
| 2013/0166048 A1 | 6/2013 | Werner et al. |
| 2013/0190903 A1 | 7/2013 | Balakrishnan et al. |
| 2013/0191034 A1 | 7/2013 | Weast et al. |
| 2013/0228063 A1 | 9/2013 | Turner |
| 2013/0231574 A1 | 9/2013 | Tran |
| 2013/0238287 A1 | 9/2013 | Hoffman et al. |
| 2013/0261475 A1* | 10/2013 | Mochizuki ................... 600/493 |
| 2013/0267249 A1 | 10/2013 | Rosenberg |
| 2013/0268199 A1 | 10/2013 | Nielsen et al. |
| 2013/0268236 A1 | 10/2013 | Yuen et al. |
| 2013/0274904 A1 | 10/2013 | Coza et al. |
| 2013/0289366 A1* | 10/2013 | Chua et al. .................. 600/301 |
| 2013/0296666 A1 | 11/2013 | Kumar et al. |
| 2013/0296672 A1* | 11/2013 | O'Neil et al. ................ 600/324 |
| 2013/0296673 A1* | 11/2013 | Thaveeprungsriporn et al. .......................... 600/324 |
| 2013/0310896 A1 | 11/2013 | Mass |
| 2013/0325396 A1 | 12/2013 | Yuen et al. |
| 2013/0337974 A1* | 12/2013 | Yanev et al. ..................... 482/8 |
| 2014/0035761 A1 | 2/2014 | Burton et al. |
| 2014/0035764 A1 | 2/2014 | Burton et al. |
| 2014/0039804 A1 | 2/2014 | Park et al. |
| 2014/0039840 A1 | 2/2014 | Yuen et al. |
| 2014/0039841 A1 | 2/2014 | Yuen et al. |
| 2014/0077673 A1* | 3/2014 | Garg et al. .................... 312/237 |
| 2014/0094941 A1 | 4/2014 | Ellis et al. |
| 2014/0125618 A1 | 5/2014 | Panther et al. |
| 2014/0164611 A1 | 6/2014 | Molettiere et al. |
| 2014/0213858 A1* | 7/2014 | Presura et al. ................. 600/301 |
| 2014/0275885 A1* | 9/2014 | Isaacson et al. ............. 600/324 |
| 2014/0316305 A1 | 10/2014 | Venkatraman et al. |

FOREIGN PATENT DOCUMENTS

| | | |
|---|---|---|
| WO | WO 2008038141 | 4/2008 |
| WO | WO 2009042965 | 4/2009 |

OTHER PUBLICATIONS

"Activity Classification Using Realistic Data From Wearable Sensors", Parkka, et al, IEEE Transactions on Information Technology in Biomedicine, vol. 10, No. 1, Jan. 2006, pp. 119-128.

"Altimeter and Barometer System", Clifford, et al., Freescale Semiconductor Aplication Note AN1979, Rev. 3, Nov. 2006.

"An Intelligent Multi-Sensor system for Pedestrian Navigation", Retscher, Journal of Global Positioning Systems, vol. 5, No. 1, 2006, pp. 110-118.

"Automatic classification of ambulatory movements and evaluation of energy consumptions utilizing accelerometers and barometer", Ohtaki, et al, Microsystem Technologies, vol. 11, No. 8-10, Aug. 2005, pp. 1034-1040.

(56) References Cited

OTHER PUBLICATIONS

"Classification of Human Moving Patterns Using Air Pressure and Acceleration", Sagawa, et al, Proceedings of the 24th Annual Conference of the IEEE Industrial Electronics Society, vol. 2, Aug.-Sep. 1998, pp. 1214-1219.

"Design of a Wireless Assisted Pedestrian Dead Reckoning System—The NavMote Experience", Fang, et al, IEEE Transactions on Instrumentation and Measurement, vol. 54, No. 6, Dec. 2005, pp. 2342-2358.

"Direct Measurement of Human Movement by Accelerometry", Godfrey, et al., Medical Engineering & Physics, vol. 30, 2008, pp. 1364-1386.

"Drift-free dynamic height sensor using MEMS IMU aided by MEMS pressure sensor", Tanigawa, et al, Workshop on Positioning, Navigation and Communication, Mar. 2008, pp. 191-196.

"Evaluation of a New Method of Heading Estimation of Pedestrian Dead Reckoning Using Shoe Mounted Sensors", Stirling et al., Journal of Navigation, vol. 58, 2005, pp. 31-45.

"Foot Mounted Inertia System for Pedestrian Naviation", Godha et al., Measurement Science and Technology, vol. 19, No. 7, May 2008, pp. 1-9.

"Improvement of Walking Speed Prediction by Accelerometry and Altimetry, Validated by Satellite Positioning", Perrin, et al, Medical & Biological Engineering & Computing, vol. 38, 2000, pp. 164-168.

"Indoor Navigation with MEMS Sensors", Lammel, et al., Proceedings of the Eurosensors XIII conference, vol. 1, No. 1, Sep. 2009, pp. 532-535.

"Non-restricted measurement of walking distance", Sagawa, et al, IEEE Int'l Conf. on Systems, Man, and Cybernetics, vol. 3, Oct. 2000, pp. 1847-1852.

"On Foot Navigation: When GPS alone is not Enough", Ladetto, et al, Journal of Navigation, vol. 53, No. 2, Sep. 2000, pp. 279-285.

"SCP 1000-D01/D11 Pressure Sensor as Barometer and Altimeter", VTI Technologies Application, Jun. 2006, Note 33.

"Suunto LUMI User Guide", Jun. and Sep. 1997.

"Using MS5534 for altimeters and barometers", Intersema App., Note AN501, Jan. 2006.

"Validated caloric expenditure estimation using a single body-worn sensor", Lester, et al, Proc. of the Int'l Conf. on Ubiquitous Computing, 2009, pp. 225-234.

Deepak et al., Plug-and-Play, Single-Chip Photoplethysmography, 34th Annual International Conference of the IEEE EMBS, San Diego, California USA, Aug. 28-Sep. 1, 2012, 4 pages. Jun. 12, 2014 9:37:30 AM PDT No No.

International Search Report issued on Aug. 15, 2008, in related application PCT/IB07/03617.

* cited by examiner

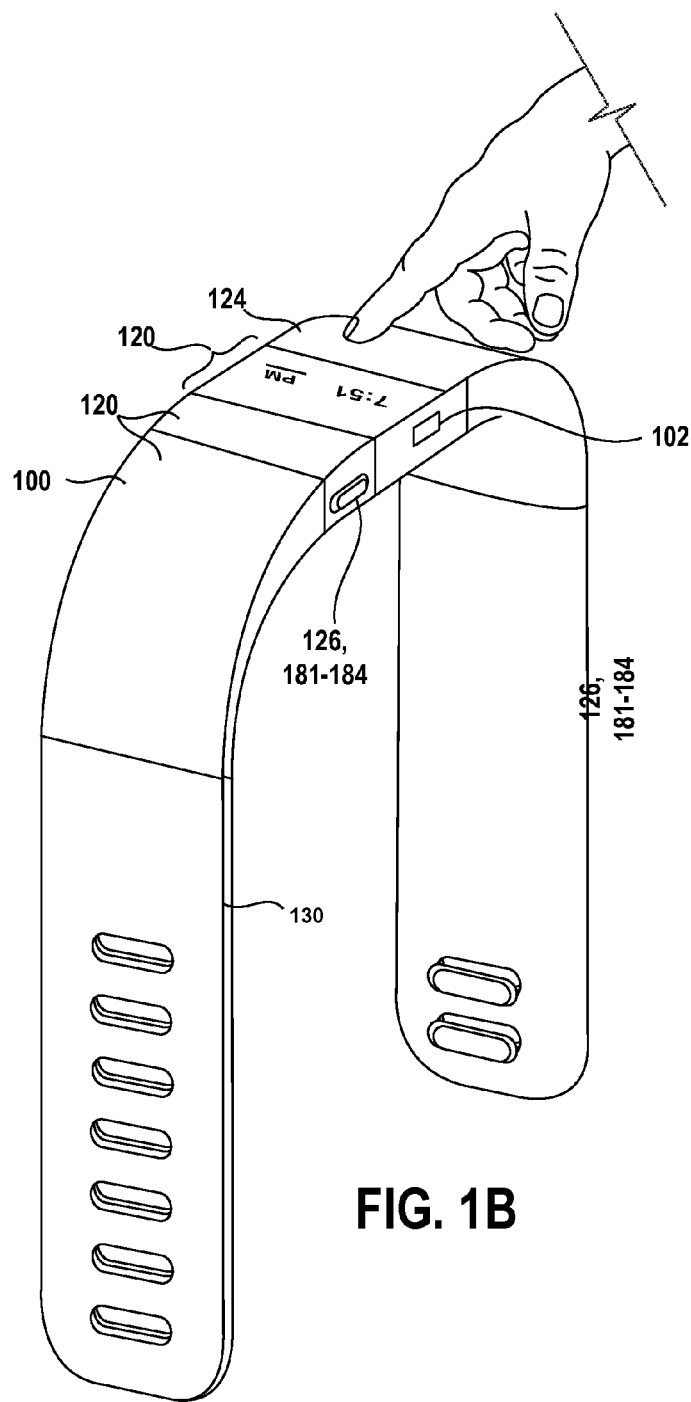
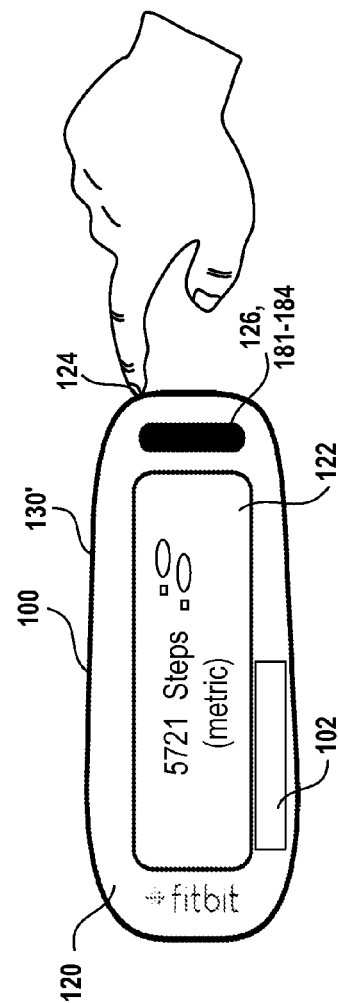
FIG. 1B
FIG. 1C

METHODS, SYSTEMS AND DEVICES FOR MEASURING FINGERTIP HEART RATE

CROSS REFERENCE TO RELATED APPLICATIONS

This application is a continuation of and claims priority from co-pending U.S. patent application Ser. No. 14/156,381, filed on Jan. 15, 2014 and entitled "Methods, Systems and Devices for Measuring Fingertip Heart Rate," which is incorporated herein by reference in its entirety. This application also claims priority from U.S. Provisional Patent Application No. 61/924,547 filed on Jan. 7, 2014 and entitled "Methods, Systems and Devices for Measuring Fingertip Heart Rate," which is incorporated herein by reference in its entirety. This application also claims priority, through application Ser. No. 14/156,381, from U.S. Provisional Patent Application No. 61/752,826 filed on Jan. 15, 2013 and entitled "Portable Monitoring Devices and Methods of Operating Same," which is incorporated herein by reference in its entirety. This application also claims priority through application Ser. No. 14/156,381, from U.S. Provisional Patent Application No. 61/830,600 filed on Jun. 3, 2013 and entitled "Portable Monitoring Devices and Methods of Operating Same," which is incorporated herein by reference in its entirety.

BACKGROUND

The present disclosure relates to systems and methods for capturing bodily activity and synchronizing data transfers between a capture device and a client device.

In recent years, the need for health and fitness has grown tremendously. The growth has occurred due to a better understanding of the benefits of good fitness to overall health and wellness. Unfortunately, although today's modern culture has brought about many new technologies, such as the Internet, connected devices and computers, people have become less active. Additionally, many office jobs require people to sit in front of computer screens for long periods of time, which further reduces a person's activity levels. Furthermore, much of today's entertainment options involve viewing multimedia content, computer social networking, and other types of computer involved interfacing. Although such computer activity can be very productive as well as entertaining, such activity tends to reduce a person's overall physical activity.

To provide users concerned with health and fitness a way of measuring or accounting for their activity or lack thereof, fitness trackers are often used. Fitness trackers are used to measure activity, such as walking, motion, running, sleeping, being inactive, bicycling, exercising on an elliptical trainer, and the like. Usually, the data collected by such fitness trackers can be transferred and viewed on a computing device. However, such data is often provided as a basic accumulation of activity data with complicated or confusing interfaces. In addition, updates between a tracker and a client device usually require wired connectors and/or complex syncing schemes.

It is in this context that embodiments described herein arise.

SUMMARY

Broadly speaking, the present invention fills these needs by providing a system and method for detecting and measuring a user's heart rate. It should be appreciated that the present invention can be implemented in numerous ways, including as a process, an apparatus, a system, computer readable media, or a device. Several inventive embodiments of the present invention are described below.

One embodiment provides an activity tracking device having a motion sensor and a processor in a housing. The processor configured for processing motion data produced by the motion sensor. A display screen is integrated with the housing to display metrics that quantify the motion data produced by the motion sensor. A light source is integrated within the housing to enable light to be directed out of the housing at a heart rate monitor location on the housing and a light detector is integrated within the housing. The light detector configured to capture an amount of the light that is reflected back to the light detector, at least a first portion of the light reflected back to the light detector is reflected from a blood vessel under a skin of a user when the user places the skin over the heart rate monitor location on the housing. The processor is also in communication with the light detector to process the reflected light to identify heart beats of the user and produce an indication of a heart rate that can be displayed on the display screen, as an option, in addition to the metrics that quantify the motion data.

The processor can differentiate between a baseline light scattering and reflectance signal detected between the each one of multiple heart beats and a second light scattering and reflectance signal corresponding to at least one heart beat in the blood vessel. The second reflectance signal being less than the baseline reflectance signal, where the blood vessel scatters more of the light during the at least one heart beat than between each one of the multiple heart beats.

The motion sensor can be one of or include an accelerometer, or a global positioning sensor, or a magnetometer, or a gyroscope, or a rotary encoder, or a calorie measurement sensor, or a moisture measurement sensor, or a displacement sensor, or an ultrasonic sensor, or a pedometer, or an altimeter, or a linear motion sensor, or an angular motion sensor, or a multi-axis motion sensor, or a combination of two or more thereof.

The activity tracking device can also include a communication transceiver configured for communicating via at least one a wireless network, an ambient light sensor, an indicator for visually identifying the heart rate monitor location on the housing and at least one infrared (IR) proximity sensor associated with the light source and light detector. The IR proximity sensor can be configured to activate the light source and light detector upon detecting presence of the skin of the user. Detecting presence of the skin of the user can also function to navigate to one or more metrics of the display screen.

The activity tracking device can also include a pressure detecting system configured for detecting a pressure applied to the heart rate monitor location on the housing with the skin of the user during the identification of heart beats. The activity tracking device can output at least one a feedback signal regarding the detected pressure applied to the heart rate monitor location, the feedback indication being indicative of more or less pressure desired to produce the heart rate, the feedback signal including at least one of a visual signal, a graphic signal, a tactile signal, and an audible signal. The pressure detecting system can include at least one of processing of the reflected light to identify one of an excess pressure, an insufficient pressure or an acceptable pressure from the detected heart beats of the user, or a pressure sensor in the button.

The activity tracking device can also include a display of one or both of waveform data or numerical data when the skin of the user is over the heart rate monitor location and the heart beats are being identified over a sampling time period and upon concluding the sampling time period, displaying the heart rate on the display screen. At least one recalled heart rate can be displayed on the display screen. The light detector can be disposed next to the light source.

The heart rate can be calculated based on an algorithm that detects multiple heart beats in the light received in the light detector within a sampling time period, measures a first time interval between a first beat of the detected heart beats and a second beat of the detected heart beats and divides the sample time interval by the first time interval to determine a first estimate of heart beats detected within the sampling time period. The first estimate of heart beats is extrapolated within the sampling time period to a first estimated heart beats per minute and the first estimate heart beats per minute is output to the display screen.

The heart rate can be calculated based on an algorithm that adds at least one beat to the first estimate of heart beats to produce a second estimate of heart beats and subtracts at least one beat from the first estimate of beats to produce a third estimate of heart beats. The first estimate of heart beats, the second estimate of heart beats and the third estimate of heart beats are scored and a highest scoring estimate of heart beats is selected and output to the display screen.

The light source and the reflected light detector can be selected for any suitable wavelength or suitable band of wavelengths of light ranging from between infrared wavelengths through a human visible spectrum to ultraviolet wavelengths. The light source includes at least one of an infrared (IR) light source, wherein the IR light emitted from the light source produces a deadfront at the heart rate monitor location of the housing or a green light source and the heart rate monitor location includes a translucent green window.

The heart rate monitor location includes a cover that enables infrared (IR) light of the light source or any other wavelength of light from the light source to pass while blocking substantially all light in a human visible spectrum. The light source and light detector can additionally function as a proximity sensor to activate the display screen. The heart rate monitor location can include a button. The button can have an infrared (IR) light transmitting structure. The light source and the light detector can be disposed substantially below the button. The button can also function to navigate to one or more metrics of the display screen. The functions to navigate can be enabled while the heart beats are measured. The skin can be of a finger of a user.

Another embodiment provides a method of tracking activity including sensing motion with a motion sensor, the motion sensor including a processor. The processor is configured for processing motion data produced by the motion sensor. Metrics that quantify the motion data produced by the motion sensing can be displayed on a device display screen integrated with a housing of the motion sensor. A directed light is emitted from a light source, the light source being included in the housing at a heart rate monitor location on the housing and an amount of the light that is reflected back to a light detector is captured by the light detector integrated within the housing. At least a first portion of the light reflected back to the light detector is reflected from a blood vessel disposed under a skin of a user when the user places the skin over the heart rate monitor location on the housing. The processor further being in communication with the light detector to enable processing of the reflected light to identify heart beats of the user and produce an indication of a heart rate. The indication of the heart rate being displayable on the display screen as an option, in addition to the metrics that quantify the motion data.

The method can also include detecting a pressure applied to the heart rate monitor location of the housing with the skin of the user during the identification of heart beats, the pressure being detected by a pressure detecting system included in the housing and outputting a feedback signal regarding the detected pressure applied to the heart rate monitor location, the feedback indication being indicative of more or less pressure desired to produce the heart rate. One or both of waveform data or numerical data can be displayed when the skin of the user is over the heart rate monitor location and the heart beats are being identified over a sampling time period. The heart rate can be displayed on the display screen upon concluding the sampling time period.

Yet another embodiment provides a heart rate monitor including a light source and a light detector disposed to receive light emitted from the light source and reflected from a blood vessel disposed within in a heart rate monitor subject. A display screen and a processor coupled to the light source, the light detector and the display screen, are also included.

Still another embodiment provides an activity tracking device including a housing including a motion sensor and a processor. The processor is configured for processing motion data produced by the motion sensor. A display screen is integrated with the housing to display metrics that quantify the motion data produced by the motion sensor. A light source is also integrated within the housing to enable light to be directed out of the housing at a heart rate monitor location on the housing and a light detector is integrated within the housing. The light detector is configured to capture an amount of the light that is reflected back to the light detector. At least a first portion of the light reflected back to the light detector is reflected from a blood vessel disposed under a skin of a user when the user places the skin over the heart rate monitor location on the housing. The processor is also in communication with the light detector to enable processing of the reflected light to identify heart beats of the user and produce an indication of a heart rate that can be displayed on the display screen, as an option, in addition to the metrics that quantify the motion data. Other aspects and advantages of the invention will become apparent from the following detailed description, taken in conjunction with the accompanying drawings, illustrating by way of example the principles of the invention.

BRIEF DESCRIPTION OF THE DRAWINGS

The present invention will be readily understood by the following detailed description in conjunction with the accompanying drawings.

FIG. 1B illustrates an example of an activity tracking device having a housing in the form of a wearable wrist attachable device.

FIG. 1C illustrates another example of an activity tracking device, in accordance with embodiments of the present invention.

DETAILED DESCRIPTION

Figure 1A:
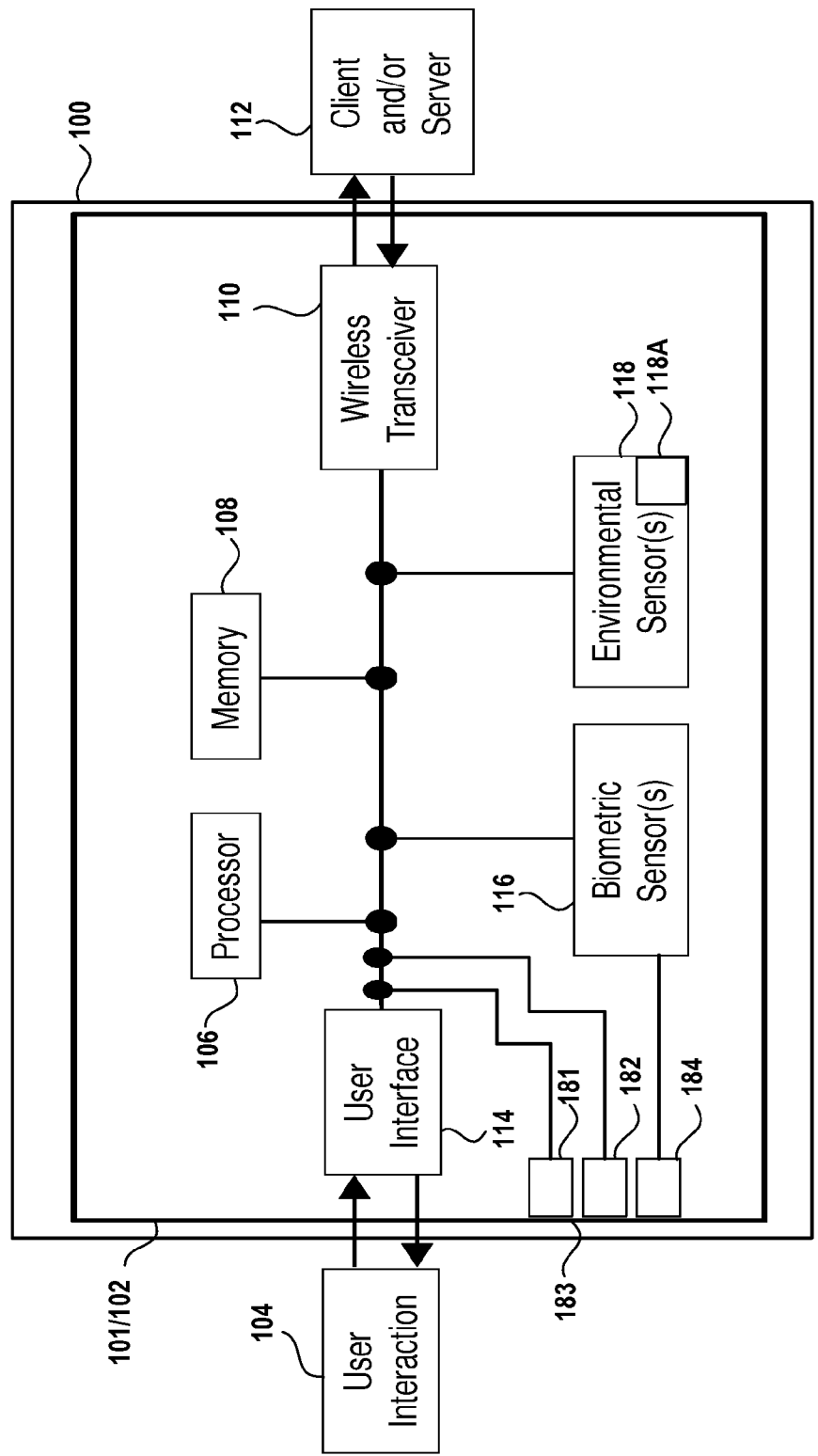
FIG. 1A shows a block diagram of an activity tracking device, in accordance with embodiments of the present invention

Several exemplary embodiments for activity tracking devices and methods capable monitoring and displaying both a user's activities and the user's heart rate will now be described. It will be apparent to those skilled in the art that the present invention may be practiced without some or all of the specific details set forth herein.

The user's heart rate can be measured by directing a light of a suitable wavelength into a user's skin and capturing a portion of the light reflected from a user's blood vessel inside the user's body. The reflected light includes data corresponding to the user's heart beats. Using this heart beat data and filtering methods and systems provide a rapid, accurate measurement of the user's heart rate. Thereby allowing the user to monitor both his activity and his heart rate. Motion data from a motion sensor within the activity tracking device can be used to identify false heart beats and provide a more accurate heart rate indication to the user, even while the user is engaged in a rigorous activity.

Embodiments described in the present disclosure provide systems, apparatus, computer readable media, and methods for analyzing tracked activity data and providing navigation screens and interfaces. Some embodiments are directed to providing navigation interfaces for an activity tracking device. The activity tracking device includes sensors for detecting when physical contact occurs onto the activity tracking device and logic for providing a display action to the screen of the activity tracking device. The physical contact, in one embodiment, can be qualified as an input when the physical contact has a particular characteristic that is predefined. The characteristic can be, when the contact is the result of one or more taps, e.g., physical contact to the activity tracking device by a finger or hand of the user, or object held by a user and used to impart the contact.

In other embodiments, the input can be non-physical, such as proximity sensing input. The proximity sensing input can be processed by an infrared proximity sensor, a thermal sensor, etc. The input can also be by way of a button, voice input, gaze detected input, input processed in response to motion or motion profiles, etc.

It should be noted that there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Further, in the course of describing and illustrating the present inventions, various circuitry, architectures, structures, components, functions and/or elements, as well as combinations and/or permutations thereof, are set forth. It should be understood that circuitry, architectures, structures, components, functions and/or elements other than those specifically described and illustrated, are contemplated and are within the scope of the present inventions, as well as combinations and/or permutations thereof.

FIG. 1A shows a block diagram of an activity tracking device 100, in accordance with embodiments of the present invention. The activity tracking device 100 is contained in a housing 101, which may be worn or held by a user. The housing 101 may be in the form of a wristband, a clip on device, a wearable device, or may be held by the user either in the user's hand or in a pocket or attached to the user's body. The activity tracking device 100 includes device components 102, which may be in the form of logic, storage, and glue logic, one or more processors, microelectronics, and interfacing circuitry. In one example, the components 102 will include a processor 106, memory 108, a wireless transceiver 110, a user interface 114, biometric sensors 116, and environmental sensors 118.

The environmental sensors 118 may be in the form of motion detecting sensors 118A. In some embodiments, a motion sensor 118A can be one or more of an accelerometer, or a gyroscope, or a rotary encoder, or a calorie measurement sensor, or a heat measurement sensor, or a moisture measurement sensor, or a displacement sensor, or an ultrasonic sensor, or a pedometer, or an altimeter, or a linear motion sensor, or an angular motion sensor, or a multi-axis motion sensor, or a combination thereof.

The biometric sensors 116 can be defined to measure physiological characteristics of the user that is using the activity tracking device 100. The user interface 114 provides a way for communicating with the activity tracking device 100, in response to user interaction 104. The user interaction 104 can be in the form of physical contact (e.g., without limitation, tapping, sliding, rubbing, multiple taps, gestures, etc.). The biometric sensors 116 can be a one or more proximity sensors 184 capable of detecting the user's presence or touch within a predefined distance or proximity. The proximity sensor 184 can be an infrared (IR) proximity sensor associated with the light source 181 and light detector 182, the IR proximity sensor configured to activate the light source and light detector upon detecting presence of the skin of the user.

The light source 181 and the light detector 182 are located near the external surface of the activity tracking device 100 at a heart rate monitor location 183. The heart rate monitor location 183 can include an indicator such as a marking or an image so the user can easily identify the heart rate monitor location 183. The marking or image can be a raised dot or dimple or a depression or an image of the fingerprint or the heart or any other suitable indication of the heart rate monitor location 183. The heart rate monitor location 183 can include a cover that enables infrared (IR) light of the light source 181 to pass while blocking substantially all light in a human visible spectrum. The heart rate monitor location 183 can include the button 126 or be separate from the button. In one embodiment, the button 126 has an infrared (IR) light transmitting structure and the light source 181 and the light detector 182 are disposed below the button, inside the housing. The button 126 can also provide navigation functions to one or more metrics of the display screen 122.

In some embodiments, the user interface 114 is configured to receive user interaction 104 that is in the form of noncontact input. The noncontact input can be by way of one or more proximity sensors 184, button presses, touch sensitive screen inputs, graphical user interface inputs, voice inputs, sound inputs, etc. The activity tracking device 100 can communicate with a client and/or server 112 using the wireless transceiver 110. The wireless transceiver 110 will allow the activity tracking device 100 to communicate using a wireless connection, which is enabled by wireless communication logic. The wireless communication logic can be in the form of a circuit having radio communication capabilities. The radio communication capabilities can be in the form of a Wi-Fi connection, a Bluetooth connection, a low-energy Bluetooth connection, or any other form of wireless tethering or near field communication. In still other embodiments, the activity tracking device 100 can communicate with other computing devices using a wired connection (not shown). As mentioned, the environmental sensors 118 can detect motion of the activity tracking device 100.

The motion can be activity of the user, such as walking, running, stair climbing, etc. The motion can also be in the form of physical contact received on any surface of the activity tracking device 110, so long as the environmental sensors 118 can detect such motion from the physical contact. As will be explained in more detail below, the physical contact may be in the form of a tap or multiple taps by a finger upon the housing of the activity tracking device 100.

FIG. 1B illustrates an example of an activity tracking device 100 having a housing 130 in the form of a wearable wrist attachable device. The sensors of the activity tracking device 100 can, as mentioned above, detect motion such as physical contact that is applied and received on a surface 120 of the housing 130. In the example shown, the physical contact 124 is in the form of a tap or multiple taps on the surface 120. Device components 102 are, in one embodiment, contained within the housing 130. The location at which the device components 102 are integrated into the housing 130 can vary. For example, the device components 102 can be integrated throughout various locations around the housing 130, and not limited to the central portion of the wrist attachable device. In some embodiments, the device components 102 can be integrated into or with a smart watch device.

In other embodiments, the device components 102 are positioned substantially in a central position of the wrist attachable device, such as under or proximate to a location where a display screen 122 is located. In the illustrated example, the housing 130 also includes a button 126. The button 126 can be pressed to activate the display screen 122, navigate to various metrics displayed on the screen 122, or turn off the screen 122.

FIG. 1C illustrates another example of an activity tracking device 100, in accordance with embodiments of the present invention. The form factor of the activity tracking device 100 is shown as a clickable device that includes a screen 122, a button 126, and device components 102 integrated within the housing 130'. The housing 130' can include a clip that allows for attachment to clothing or articles of the user, or to simply place the device within a pocket or holder of the user. Accordingly, the physical contact 124 such as a touch or a tap, as shown with respect to FIG. 1B, can also be implemented upon the surface 120 of activity tracking device 100 of FIG. 1C. It should be understood, therefore, that the form factor of the activity tracking device 100 can take on various configurations and should not be limited to the example configurations provided herein.

Figure 2A:
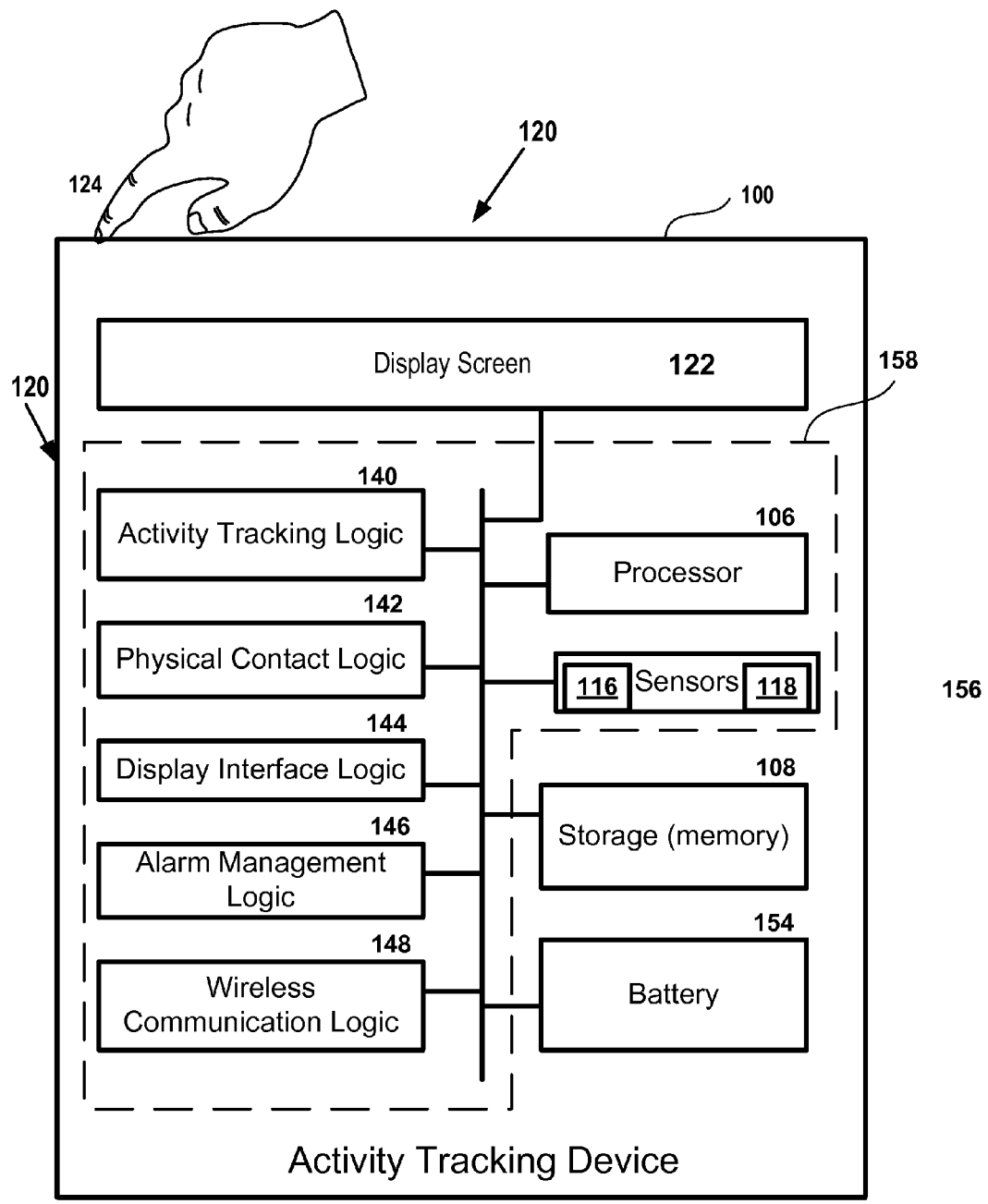
FIG. 2A illustrates an example of activity tracking device of FIG. 1A, showing some additional example components utilized for tracking activity and motion of the device, and associated interfaces to display screen.

FIG. 2A illustrates an example of activity tracking device 100 of FIG. 1A, showing some additional example components utilized for tracking activity and motion of the device, and associated interfaces to display screen 122. In this example, the finger of a user can be used to tap and provide physical contact 124 onto any surface 120 of activity tracking device 100. The physical contact, when sensed by sensors 184 of the activity tracking device 100, will cause a response by the activity tracking device 100, and therefore provide some metric on the display screen 122. In one embodiment, examples of a display screen 122 can include, but are not limited to, liquid crystal display (LCD) screens, light emitting diode (LED) screens, organic light emitting diode (OLED) screens, plasma display screens, etc.

As shown in FIG. 2A, the activity tracking device 100 includes logic 158. Logic 158 may include activity tracking logic 140, physical contact logic 142, display interface logic 144, alarm management logic 146, wireless communication logic 148, processor 106, and sensors 184. Additionally, storage (e.g. memory) 108, and a battery 154 can be integrated within the activity tracking device 100. The activity tracking logic 140 can include logic that is configured to process motion data produced by motion sensors 118, so as to quantify the motion and produce identifiable metrics associated with the motion.

Some motions will produce and quantify various types of metrics, such as step count, stairs climbed, distance traveled, very active minutes, calories burned, etc. The physical contact logic 142 can include logic that calculates or determines when particular physical contact can qualify as an input. To qualify as an input, the physical contact detected by biometric sensors 116 should have a particular pattern that is identifiable as input. For example, the input may be predefined to be a double tap input, and the physical contact logic 142 can analyze the motion to determine if a double tap indeed occurred in response to analyzing the sensor data produced by sensors 116, 118.

In other embodiments, the physical contact logic can be programmed to determine when particular physical contacts occurred, the time in between the physical contacts, and whether the one or more physical contacts will qualify within predefined motion profiles that would indicate that an input is desired. If physical contact occurs that is not within some predefined profile or pattern, the physical contact logic will not indicate or qualify that physical contact as an input.

The display interface logic 144 is configured to interface with the processor and the physical contact logic to determine when specific metric data will be displayed on the display screen 122 of the activity tracking device 100. The display interface logic 144 can act to turn on the screen, display metric information, display characters or alphanumeric information, display graphical user interface graphics, or combinations thereof. Alarm management logic 146 can function to provide a user interface and settings for managing and receiving input from a user to set an alarm. The alarm management logic can interface with a timekeeping module (e.g., clock, calendar, time zone, etc.), and can trigger the activation of an alarm. The alarm can be in the form of an audible alarm or a non-audible alarm.

A non-audible alarm can provide such alarm by way of a vibration. The vibration can be produced by a motor integrated in the activity tracking device 100. The vibration can be defined to include various vibration patterns, intensities, and custom set patterns. The vibration produced by the motor or motors of the activity tracking device 100 can be managed by the alarm management logic 146 in conjunction with processing by the processor 106. The wireless communication logic 148 is configured for communication of the activity tracking device with another computing device by way of a wireless signal. The wireless signal can be in the form of a radio signal. As noted above, the radio signal can be in the form of a Wi-Fi signal, a Bluetooth signal, a low energy Bluetooth signal, or combinations thereof. The wireless communication logic can interface with the processor 106, storage 108 and battery 154 of device 100, for transferring activity data, which may be in the form of motion data or processed motion data, stored in the storage 108 to the computing device.

In one embodiment, processor 106 functions in conjunction with the various logic components 140, 142, 144, 146, and 148. The processor 106 can, in one embodiment, provide the functionality of any one or all of the logic components. In other embodiments, multiple chips can be used to separate the processing performed by any one of the logic components and the processor 106. Sensors 116, 118 can communicate via a bus with the processor 106 and/or the logic components. The storage 108 is also in communication with the bus for providing storage of the motion data processed or tracked by the activity tracking device 100. Battery 154 is provided for providing power to the activity tracking device 100.

Figure 2B:
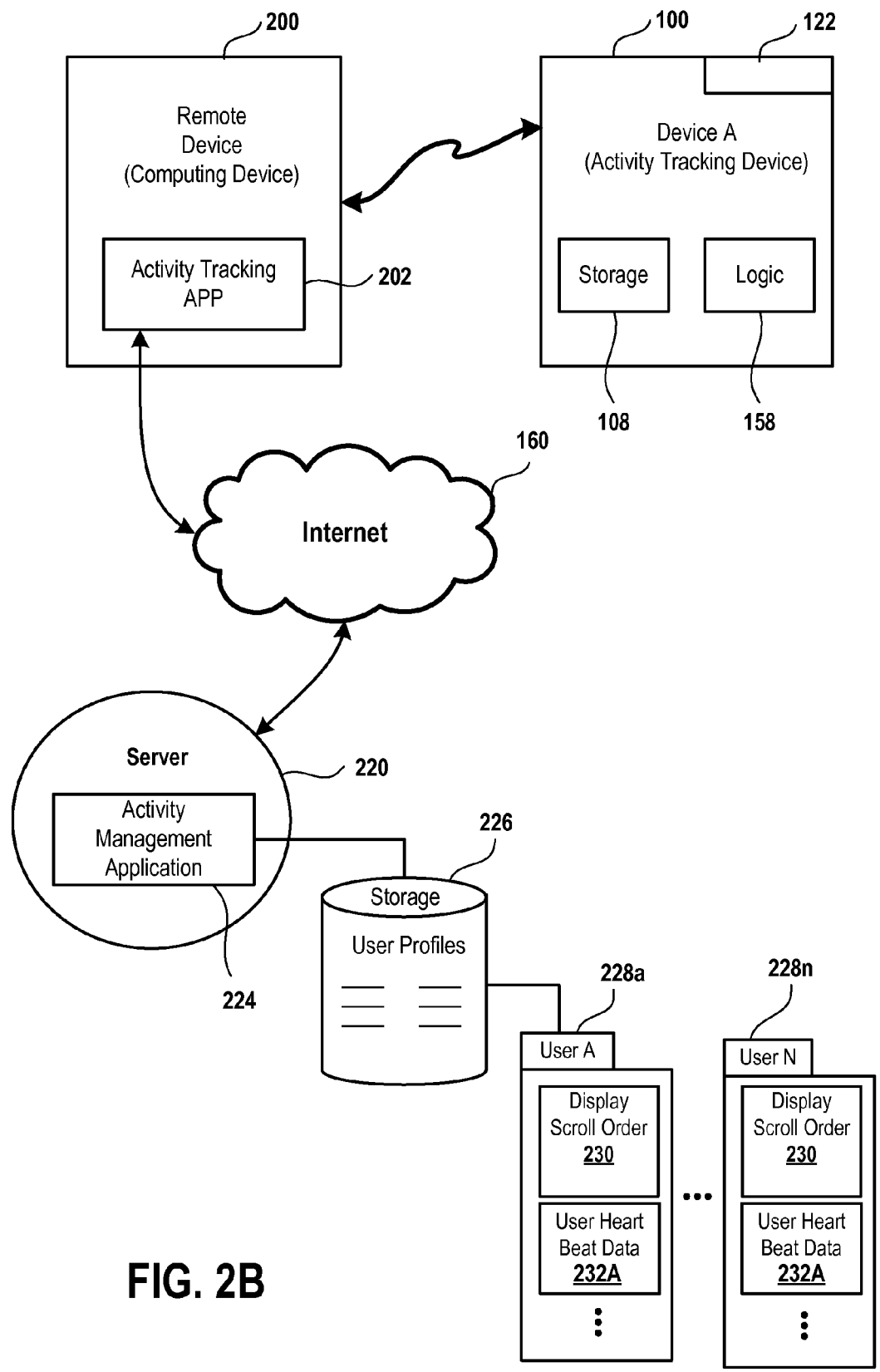
FIG. 2B illustrates an example of activity tracking device in communication with a remote device.

FIG. 2B illustrates an example of activity tracking device 100 in communication with a remote device 200. Remote device 200 is a computing device that is capable of communicating wirelessly with activity tracking device 100 and with the Internet 160. Remote device 200 can support installation and execution of applications. Such applications can include an activity tracking application 202. Activity tracking application 202 can be downloaded from a server. The server 220 can be a specialized server or a server that provides applications to devices, such as an application store. Once the activity tracking application 202 is installed in the remote device 200, the remote device 200 can communicate or be set to communicate with activity tracking device 100 (Device A). The remote device 200 can be a smartphone, a handheld computer, a tablet computer, a laptop computer, a desktop computer, or any other computing device capable of wirelessly interfacing with Device A 100 and the Internet 160.

In one embodiment, remote device 200 communicates with activity tracking device 100 over a Bluetooth connection. In one embodiment, the Bluetooth connection is a low energy Bluetooth connection (e.g., Bluetooth LE, BLE, or Bluetooth Smart). Low energy Bluetooth is configured for providing low power consumption relative to standard Bluetooth circuitry. Low energy Bluetooth uses, in one embodiment, a 2.4 GHz radio frequency, which allows for dual mode devices to share a single radio antenna. In one embodiment, low energy Bluetooth connections can function at distances up to 50 meters, with over the air data rates ranging between 1-3 megabits (Mb) per second. In one embodiment, a proximity distance for communication can be defined by the particular wireless link, and is not tied to any specific standard. It should be understood that the proximity distance limitation will change in accordance with changes to existing standards and in view of future standards and/or circuitry and capabilities.

Remote device 200 can also communicate with the Internet 160 using an Internet connection. The Internet connection of the remote device 200 can include cellular connections, wireless connections such as Wi-Fi, and combinations thereof (such as connections to switches between different types of connection links). The remote device, as mentioned above, can be a smartphone or tablet computer, or any other type of computing device having access to the Internet and with capabilities for communicating with the activity tracking device 100.

A server 220 is also provided, which is interfaced with the Internet 160. The server 220 can include a number of applications that service the activity tracking device 100, and the associated users of the activity tracking device 100 by way of user accounts. For example, the server 220 can include an activity management application 224. The activity management application 224 can include logic for providing access to various devices 100, which are associated with user accounts managed by server 220. Server 220 can include storage 226 that includes various user profiles associated with the various user accounts. The user account 228a for user A and the user account 228n for user N are shown to include various information.

The information can include, without limitation, data associated with a display scroll order 230, user data, etc. As will be described in greater detail below, the display scroll order 230 includes information regarding a user's preferences, settings, and configurations which are settable by the user or set by default at the server 220 when accessing a respective user account. The storage 226 will include any number of user profiles, depending on the number of registered users having user accounts for their respective activity tracking devices. It should also be noted that a single user account can have various or multiple devices associated therewith, and the multiple devices can be individually customized, managed and accessed by a user. In one embodiment, the server 220 provides access to a user to view the user data 232 associated with activity tracking device.

The user data 232 viewable by the user includes the tracked motion data, which is processed to identify a plurality of metrics associated with the motion data. The user data 232 viewable by the user can include user heart beat and heart rate data 232A, which is processed to identify a plurality of metrics associated with the user's heart beat.

The metrics are shown in various graphical user interfaces of a website enabled by the server 220. The website can include various pages with graphical user interfaces for rendering and displaying the various metrics for view by the user associated with the user account. In one embodiment, the website can also include interfaces that allow for data entry and configuration by the user.

The configurations can include defining which metrics will be displayed on the activity tracking device 100. In addition, the configurations can include identification of which metrics will be a first metric to be displayed on the activity tracking device. The first metric to be displayed by the activity tracking device can be in response to a user input at the activity tracked device 100. As noted above, the user input can be by way of physical contact. The physical contact is qualified by the processor and/or logic of the activity tracking device 100 to determine if the physical contact should be treated as an input. The input can trigger or cause the display screen of the activity tracking device 100 to be turned on to display a specific metric, that is selected by the user as the first metric to display. In another embodiment, the first metric displayed in response to the input can be predefined by the system as a default.

The configuration provided by the user by way of the server 220 and the activity management application 224 can also be provided by way of the activity tracking application 202 of the computing device 200. For example, the activity tracking application 202 can include a plurality of screens that also display metrics associated with the captured motion data of the activity tracking device 100. The activity tracking application 202 can also allow for user input and configuration at various graphical user interface screens to set and define which input will produce display of the first metric. In other embodiments, in addition to identifying the first metric to be displayed in response to the input, which may be physical contact, the configuration can allow an ordering of which metrics will be displayed in a specific scroll order.

In another embodiment, the scroll order of the metrics is predefined. In some embodiments, the input provided by the user by way of the physical contact can be pre-assigned to a specific metric in the scroll order. For example, the scroll order can remain the same, while the input can allow the screen to jump to a specific entry in the scroll order. Jumping to a specific entry can be viewed as a shortcut to a specific entry that is desired to be seen first by the user upon providing physical contact or input to the device 100.

Figure 3A:
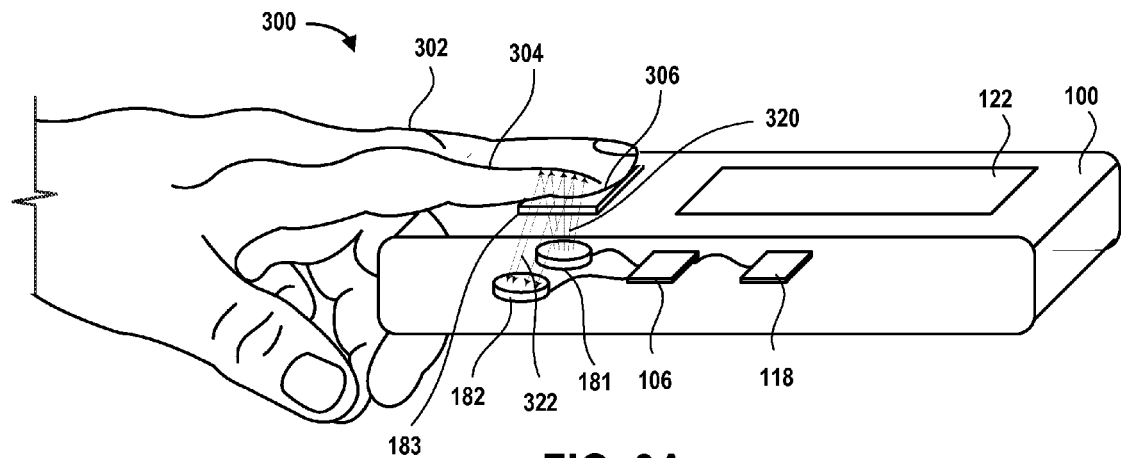
FIGS. 3A and 3B illustrate examples of activity tracking devices having a heart rate measuring system in the form of a wearable wrist attachable device, in accordance with embodiments of the present invention.
Figure 3B:
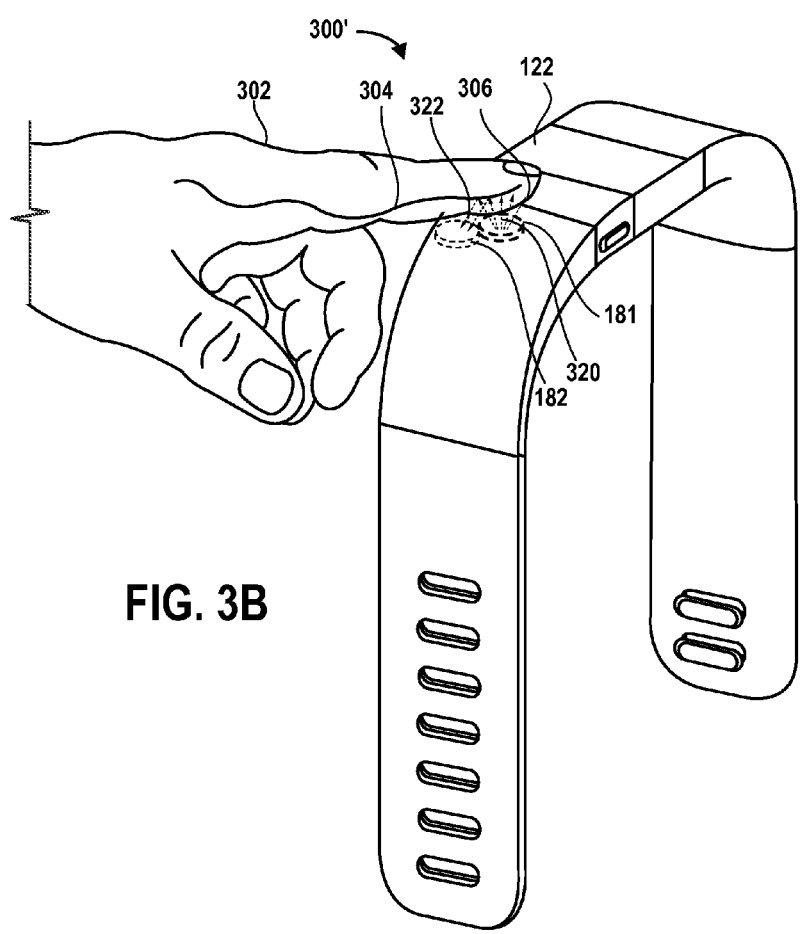

FIGS. 3A and 3B illustrate examples of activity tracking devices 300, 300' having a heart rate measuring system in the form of a wearable wrist attachable device, in accordance with embodiments of the present invention. The form factor of the activity tracking devices 300, 300' can be similar to the above activity tracking devices 100 and includes substantially similar components with the addition of the heart rate measuring system. The user's finger 302 is shown touching the activity tracking device at the heart rate monitor location 183. The light source is emitting light 320 into the user's skin 306. A portion 322 of the light 320 is reflected from the user's blood vessel 304.

Figure 3C:
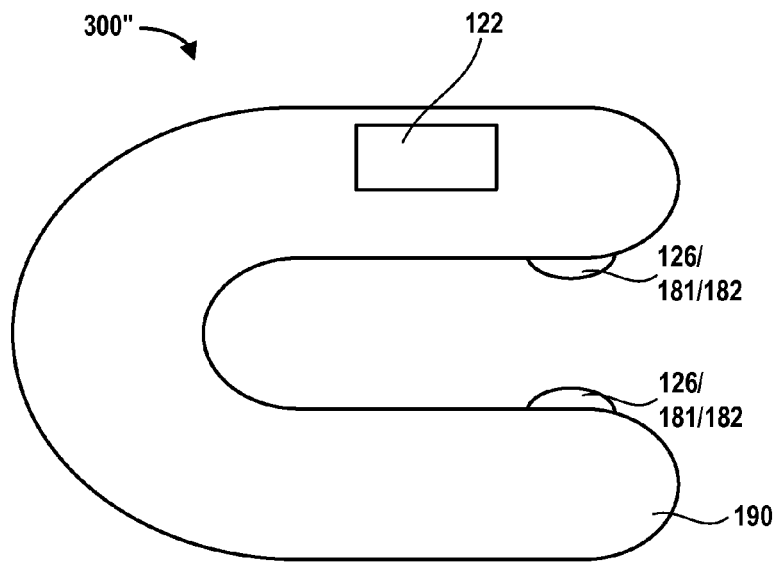
FIGS. 3C and 3D illustrate another example of an activity tracking device, in accordance with embodiments of the present invention.
Figure 3D:
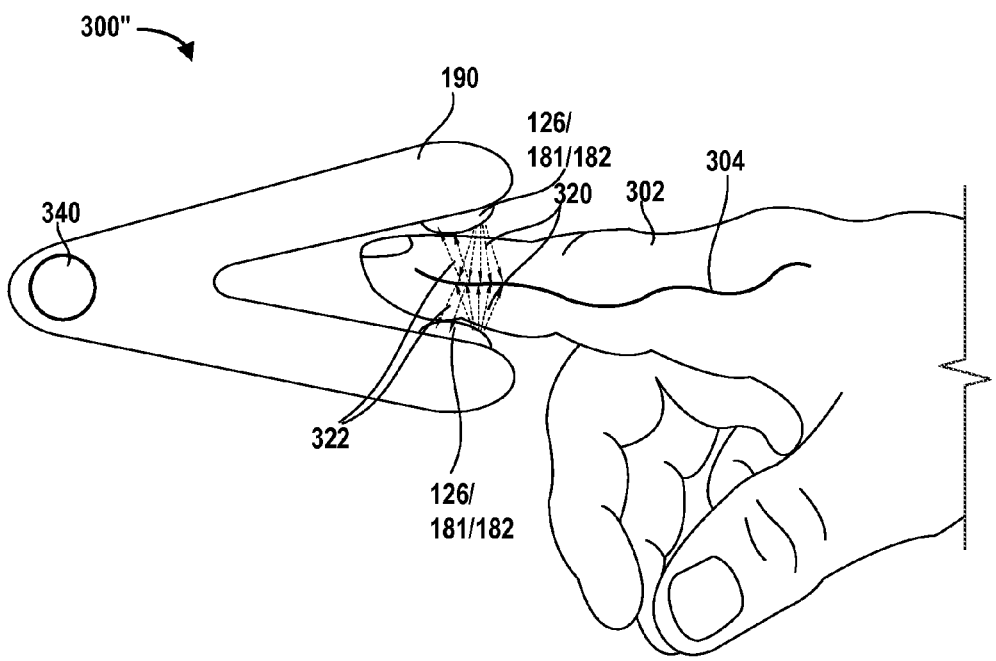

FIGS. 3C and 3D illustrate another example of an activity tracking device 300", in accordance with embodiments of the present invention. The form factor of the activity tracking device 300" is shown as a clipable device that includes a spring loaded hinge 340, a screen 122, a button 126, and device components 102 integrated within the housing 190. The housing 190 can be a shape capable of receiving a user's finger 302 and pressing down on the finger from one or both sides of the finger. Inserting the user's finger 302 can provide the physical contact or tap needed to initiate certain functions of the tracking device 100 as will be described in more detail below.

The heart rate measuring system includes a light source 181 and a reflected light detector 182. The light source 181 and the reflected light detector 182 are located close together in the activity tracking devices 300, 300', 300". In one embodiment the light source 181 and the reflected light detector 182 can be immediately adjacent. The light source 181 and the reflected light detector 182 can be included in a single package and/or a single integrated circuit. The light source 181 and the reflected light detector 182 can be selected for any one suitable wavelength or suitable band of wavelengths of light ranging from between infrared, through a human visible spectrum to ultraviolet wavelengths. The heart rate monitor location 183 can include a cover that enables light of the light source to pass while blocking substantially all light in a human visible spectrum. The cover can be a smoked filter or other suitable filter color or shaded plastic or glass or shaded glass, transparent or translucent glass or plastic or ceramic or any other suitable material capable of allowing the desired wavelengths of light to pass through the cover. In one embodiment, the light source 181 uses an infrared (IR) light and the IR light produces a deadfront at the heart rate monitor location 183. Where a deadfront is defined as a continuous surface such that the cover is not easily discernable from the remaining surface of the housing. A deadfront cover is substantially hidden from the user however a light source 181 or the display screen 122 can emits sufficient light to pass through the cover. In another embodiment, the light source 181 can be a green light and the heart rate monitor location 183 can include a translucent green window.

In operation, the user places the skin 306 of a finger tip 302 or other body part over the light source 181. The light source 181 directs the light 310 into the skin 306. The light 310 passes through the skin 306 to a blood vessel 304 such as an artery, vein, or a capillary within the finger 302. A reflected portion 312 of the light 310 is reflected from the blood vessel 304 toward the reflected light detector 182. The light detector 182 outputs a signal corresponding to the reflected portion 312 of the light. The signal is coupled to a processor 106 for processing configured to identify heart beats of the user and produce an indication of a heart rate. The indication of the heart rate can be displayed on the display screen 122.

One embodiment may use a portion of the teachings of detecting heart beats by reflecting light from a blood vessel, as taught, in part by "Plug-and-Play, Single-Chip Photoplethysmography" by Deepak Chandrasekar, et al., pages 3243-3246, presented 34th Annual International Conference of the IEEE EMBS, San Diego, Calif. USA, 28 Aug.-1 Sep. 2012 which is incorporated by reference herein for all purposes.

Chandrasekar, et al, provides in pertinent part "a digital OPS can be used as a high-performance, reflectance-mode PPG sensor . . . LED emits light into the tissue, where it experiences diffuse reflection from the tissue and capillary bed. This establishes a baseline reflectance signal which is detected at the PD. When a pulse wave propagates through the capillary bed, the reflectance signal falls slightly (0.5-5%) due to light scattering. The change is detected by the PD and processed by embedded amplification and signal processing circuitry" (Page 3244, column 1, line 34 through column 2, line 7 and FIG. 2). Where an OPS is defined as an optical proximity sensor, a PPG sensor is defined as a photoplethysmographic sensor and a PD is defined as a photodiode.

It should be understood that the teachings described by are Chandrasekar, et al only examples and other examples can include different and additional processes and systems as described in more detail throughout this disclosure. Further, Chandrasekar, et al, fails to teach suitable filtering to provide accurate hear rate indications. Further still, Chandrasekar, et al, cannot discern motion caused false heart beat detections from actual hear beat detections.

Figure 4A:
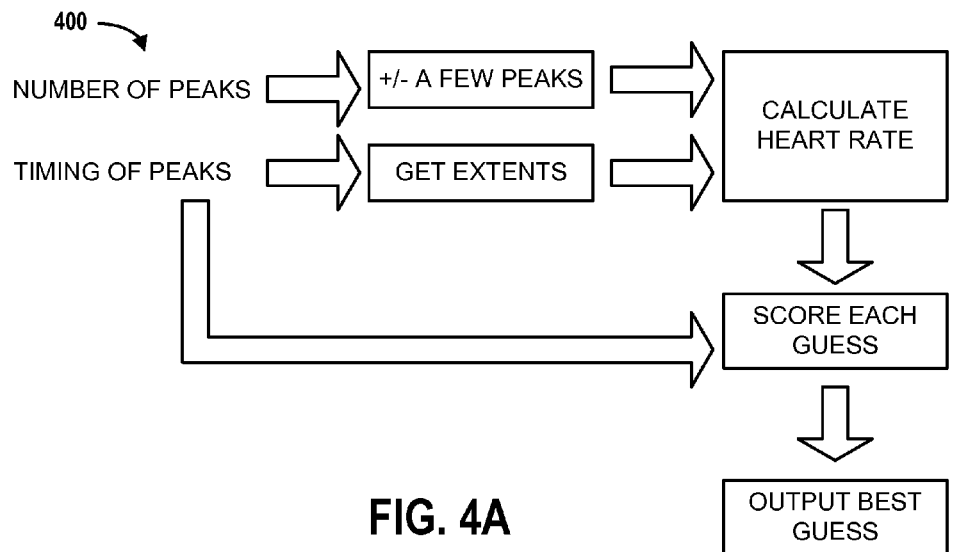
FIG. 4A is a flowchart diagram of heart rate measuring system, in accordance with embodiments of the present invention.

FIG. 4A is a flowchart diagram of heart rate measuring system, in accordance with embodiments of the present invention. The heart rate measuring system detects the heart beats and interprets the detected heart beats to peaks. The detected peaks include timing information corresponding to the time interval between the detected peaks. The detected peaks also include information of the number of detected peaks within a selected sampling time period. The sampling time period can be determined by extent peaks such as the first detected peak and the last detected peak. The number of detected peaks within the sampling time period can be used to calculate an estimated heart rate in the form of beats per minute. The timing of the detected peaks can be used to evaluate the estimated heart rate to determine a best guess of the user's actual heart rate.

Figure 4B:
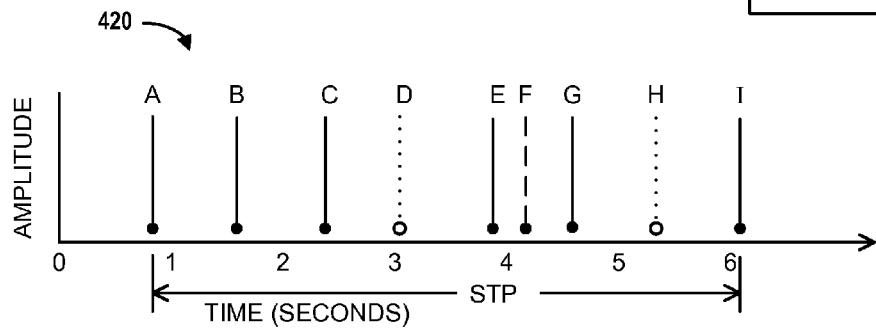
FIG. 4B is a graphical representation of an example series of peaks corresponding to detected heart beats captured during a sampling time period STP, in accordance with embodiments of the present invention.

FIG. 4B is a graphical representation 420 of an example series of peaks corresponding to detected heart beats captured during a sampling time period STP, in accordance with embodiments of the present invention. The solid line peaks A, B, C, E, G and I the dashed peak F represent the raw data detected during the sampling time period STP.

The solid line peaks A, B, C, E, G and I correspond to actual detected heart beats. The dashed peak F corresponds to a phantom beat detection. The phantom peak F can be caused by movement of the user's finger or the activity tracking device 300. The phantom peak F can be caused by noise or some other cause.

The dotted peaks D and H correspond to approximate occurrences of heart beats that should have been detected, based on the timing of the actually detected peaks A, B, C, E, G and I. The dotted peaks D and H are not actually detected peaks and are shown in the graphical representation 420 for reference purposes as will be described in more detail below.

Figure 4C:
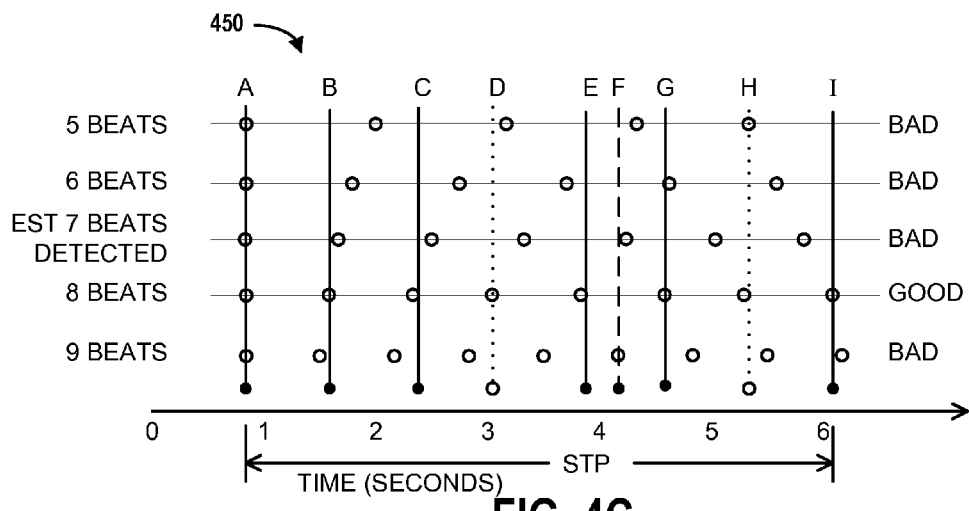
FIG. 4C is a graphical representation of the filtering process for the above example series of peaks, in accordance with embodiments of the present invention.

The raw heart beat data is next filtered to determine a best guess heart rate. FIG. 4C is a graphical representation 450 of the filtering process for the above example series of peaks, in accordance with embodiments of the present invention. The peaks A-I are transferred to FIG. 4C as a reference. Each of the horizontal lines of small circles represents a different estimate of peaks. Six actual peaks A, B, C, E, G and I correspond to six actual heart beats that were detected and one phantom peak F was detected giving a total of seven detected peaks.

Human heart beats are typically substantially evenly spaced, thus the seven detected peaks are separated by even time intervals across the sampling time period STP as shown in the estimated 7 peaks detected line. However, the filtering process evaluates the detection process to determine if the initial estimate of seven peaks is accurate as described in FIG. 5.

Figure 5:
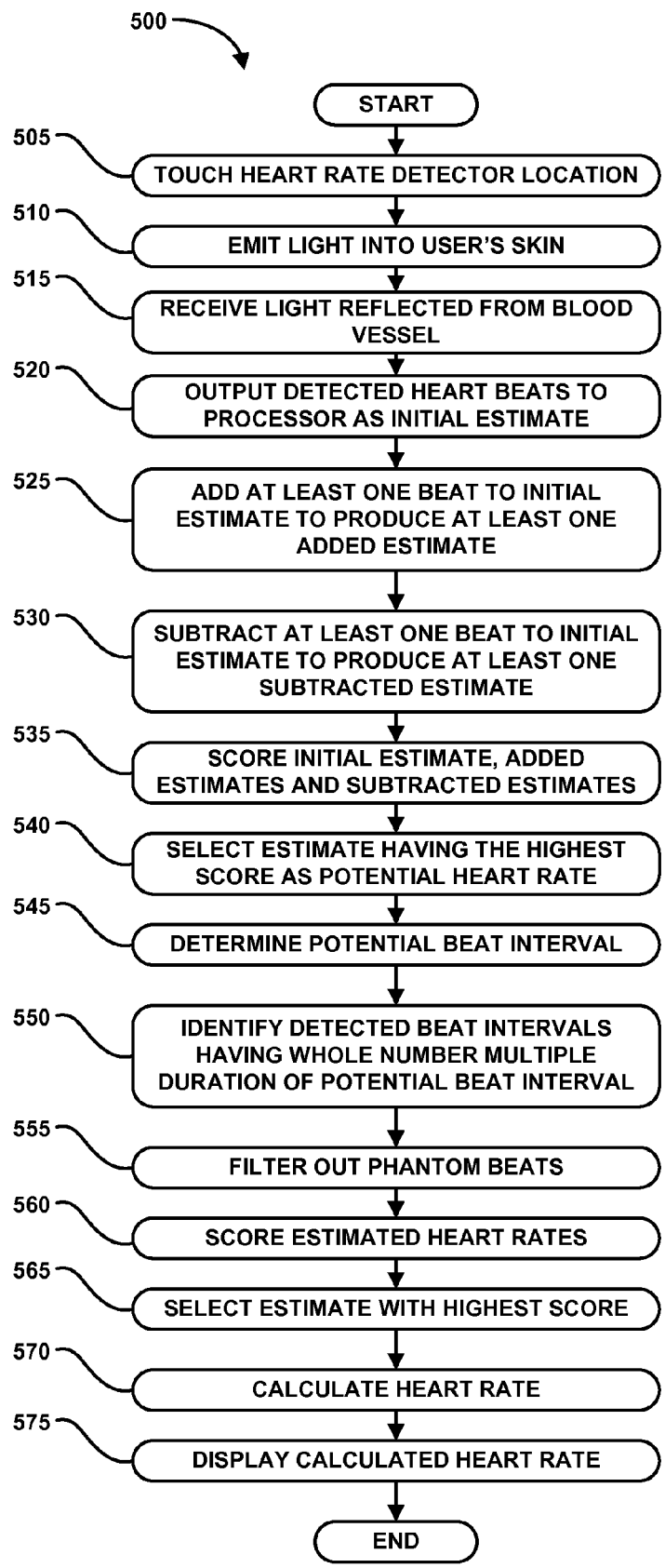
FIG. 5 is a flowchart diagram of the method operations for detecting a heart rate, in accordance with embodiments of the present invention.

FIG. 5 is a flowchart diagram of the method operations 500 for detecting a heart rate, in accordance with embodiments of the present invention. In an operation 505, the user touches the heart rate monitor location 183 and/or presses the button 126 on the activity monitor to initiate the heart rate detection. The light source 181 and detector 182 are located inside the activity tracking device near the heart rate detector heart rate monitor location 183. The heart rate monitor location 183 can include a proximity sensor and/or the button 126 as described above.

In an operation 510, the light source 181 emits a light 320 into the user's skin and at least a portion of the light 322 is reflected off of a blood vessel 304 inside the user's skin. The detector 182 receives the reflected light 322 in an operation 515 and outputs the raw data of the detected beats within a sampling time period STP, as shown in FIG. 4B, to the processor 106 in an operation 520. The raw data of the detected beats is refined and evaluated to produce a more accurate heart rate.

As shown in FIG. 4C, the initial estimate of the seven detected heart beats are illustrated as seven, evenly spaced peaks. In an operation 525 at least one beat is added to the initial estimate of seven beats to produce a corresponding at least one added estimate. In the example above two peaks are added resulting in corresponding added estimates of an eight beat estimate and a nine beat estimate. It should be understood that only one or more than two beats could be added.

In an operation 530, at least one peak is subtracted from the initial estimate of seven beats to produce a corresponding at least one subtracted estimate. In the example above two beats are subtracted resulting in corresponding subtracted estimates of a six beat estimate and a five beat estimate. It should be understood that only one or more than two beats could be subtracted. As shown in the graphical representation 450, estimated lines of beats corresponding to five, six, eight and nine peaks are shown evenly distributed across the sampling time period STP.

In an operation 535, each of the five estimated lines of beats are compared to the actually detected peaks A, B, C, E, F, G and I to determine how well each line of beats scores as most closely matching the actually detected peaks A, B, C, E, F, G and I. By way of example, the five beats estimate line closely corresponds to only actually detected peak A and phantom peak F resulting in a corresponding score of 2. Further, the six beats estimate line closely corresponds to only actually detected peaks A, E and G resulting in a corresponding score of 3. Further, the initial estimate of seven beats estimate line closely corresponds to only actually detected peaks A, B and C and phantom peak F resulting in a corresponding score of 4. The eight beats estimate line closely corresponds to peaks A, B, C, E, G and I resulting in a corresponding score of 6. Finally, the nine beats estimate line closely corresponds to peaks A, B, C and I and phantom peak F resulting in a corresponding score of 5.

In an operation 540, the eight beats estimate provides the highest score of 6 and is therefore selected as a potential heart rate for further evaluation. However, only seven peaks were detected by the heart rate monitoring system and thus the eight beats potential heart rate could be an error.

In an operation 545, intervals between the seven detected beats are measured. Recall that human heart beats are substantially evenly spaced and there are three substantially evenly spaced peaks A, B, C in the seven detected beats. The time interval between the substantially evenly spaced peaks A, B, C is selected as a potential beat interval.

In an operation 550, the potential beat interval is compared to the remaining detected beat intervals between peaks C and E, between peaks E and F, between peaks F and G, and between peaks G and I to identify any timing intervals closely corresponding to whole number multiples of the potential beat interval so as to identify missed beats. In the above example, missed peak D is found between detected peaks C and E and missed peak H is found between detected peaks G and I. The timing intervals between peaks E and F and between peaks F and G are substantially less than the potential beat interval and thus peak F is identified as a phantom peak and the phantom peak F is eliminated in an operation 555.

In an operation 560, the estimated heart beats are scored similar to the scoring in operation 535 above. The combination of the actually detected peaks A, B, C, E, G and I and the missed peaks D and H can be evaluated for each of the estimated lines of beats. The eight beats potential heart rate would yield a resulting score of 8, which would be higher than the scores of 3, 2, 3, 4 corresponding to five, six, seven and nine beats estimate lines, respectively. The eight beats potential heart rate can therefore be determined as the best guess in an operation 565.

In an operation 570, the processor 106 calculates the heart rate. The sampling time period STP is extrapolated to 60 seconds and the corresponding heart rate in heart beats per minute is output to the display screen. By way of example, the sampling time period STP is 5.2 seconds in the above example. And 60 seconds divided by 5.2 seconds is equal to 11.54. And further, 11.54 multiplied by the seven time intervals between the evenly spaced estimated eight beats yields a calculated heart rate of 81 beats per minute. In an operation 575, the processor 106 outputs the calculated heart rate to the display screen 122.

It should be noted that the heart rate measuring system can continue to detect, refine and filter the detected heart beats as long as the user's skin is in sufficiently close proximity to the light source 181 and detector 182.

Figure 6A:
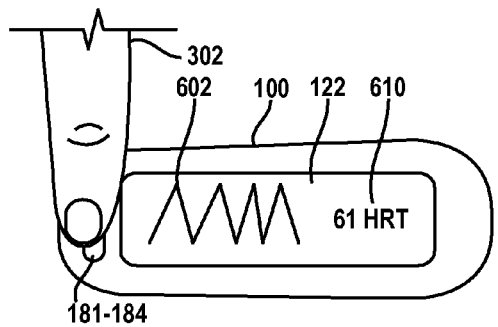
FIGS. 6A-D illustrate different presentations of the calculated heart rate on the display screen, in accordance with embodiments of the present invention.
Figure 6B:
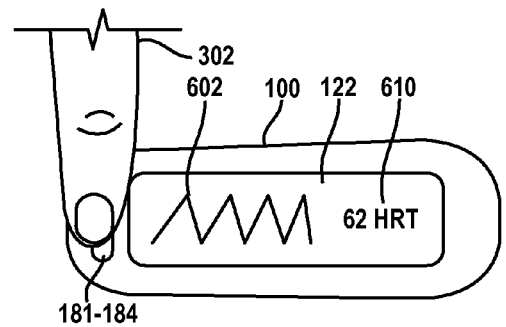
Figure 6C:
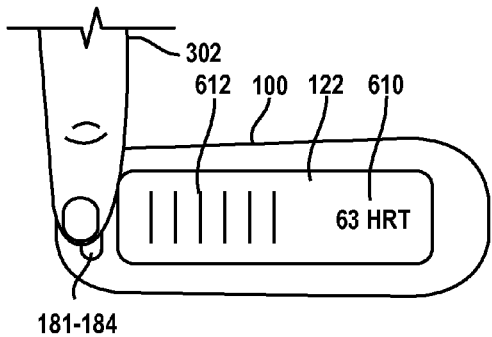
Figure 6D:
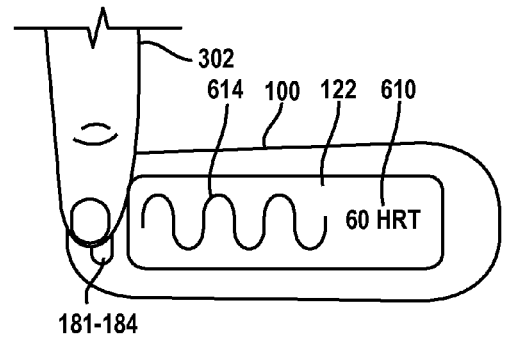

FIGS. 6A-D illustrate different presentations of the calculated heart rate on the display screen 122, in accordance with embodiments of the present invention. By way of example, in FIG. 6A the initially detected heart beats are displayed as peaks 602 and the heart rate 610 is displayed numerically "61 HRT". As the user's finger remains on the activity tracking device the heart rate is more accurately detected and the displayed heart rate 610 is updated as shown in FIG. 6B. As shown in FIG. 6C the detected heart beats are displayed as lines 612 and as a sinewave 614 in FIG. 6D. It should be noted these examples are merely some examples of displaying the user's heart rate and others examples could include flashing an icon or a portion of or the entire the display 122 or vibrating the activity tracking device in time with the detected heart beats and combinations thereof.

Figure 7A:
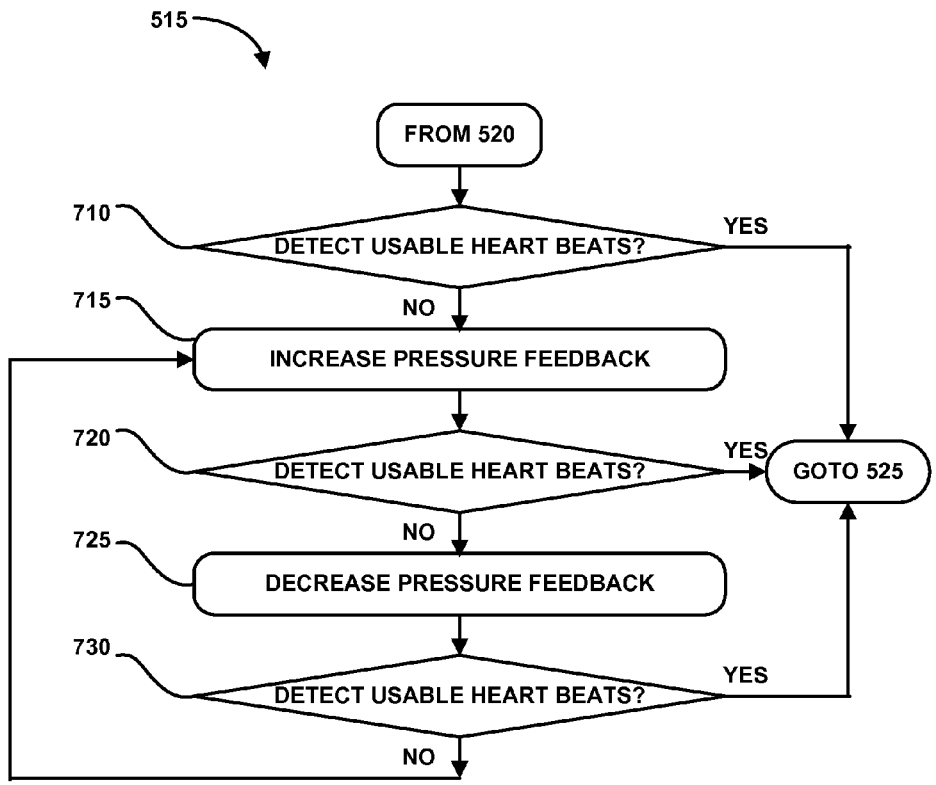
FIG. 7A is a flowchart diagram of the method operations for adjusting the user pressure on the activity tracking device while detecting a heart rate, in accordance with embodiments of the present invention.
Figure 7B:
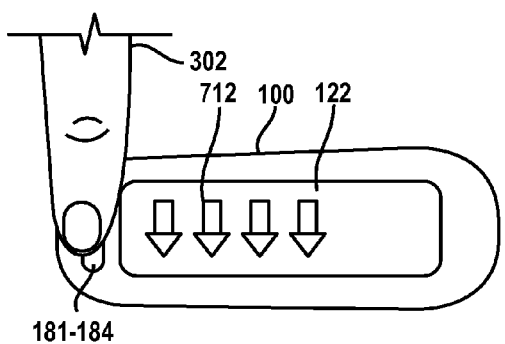
FIGS. 7B and 7C show feedback signals on the activity tracing device display, in accordance with embodiments of the present invention.
Figure 7C:
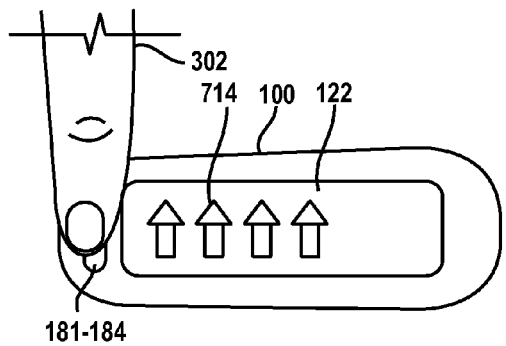

FIG. 7A is a flowchart diagram of the method operations for adjusting the user pressure on the activity tracking device while detecting a heart rate, in accordance with embodiments of the present invention. FIGS. 7B and 7C show feedback signals on the activity tracing device display, in accordance with embodiments of the present invention. The button 126 can also include a pressure sensor that can be used to determine the user's pressure on the heart rate monitor location 183. In one embodiment, the pressure sensor can include at least one of a strain gauge, a push resistance built into the button 126, or a force sensitive film under, within or on a surface of the button and combinations thereof and any other suitable pressure sensor.

Alternatively, the excessive pressure or insufficient pressure can degrade the quality of the heart beat data in the reflected light 322 to a level that the heart rate cannot be suitably monitored. Similarly, the user's motion, such as running, can interfere with and produce artifacts and false readings. The processor 106 can use the motion sensor to identify and filter out the falsely detected heart beats from the detected heart beats. By way of example, the processor can detect when the user steps down and the vibration through the user's body and identify a detected heart beat coinciding with the step as a suspected false heart beat.

From operation 520 in FIG. 5 above, the processor may determine that the detected heart beats are too erratic to accurately measure in an operation 710. The detected heart beats are too erratic can be too erratic due to pressing the user's finger too lightly or too hard on the activity tracking device. In an operation 715, a feedback to the user is provided to increase pressure on the activity tracking device. As shown in FIG. 7B the increase pressure feedback can be in the form of one or more arrows pointing down or toward the user's finger. Alternatively, the activity device can flash a portion or all of the display 122 or display words such as "press down" or icons, or vibrate or other suitable tactile feedback, visual feedback, or audible feedback to the user.

The detected heart beats are constantly monitored for usability, in an operation 720. If increasing the pressure provides usable heart beat data then the method operations return to operation 525 in FIG. 5. If increasing the pressure does not provide usable heart beat data then the method operations continue in an operation 725 where the user is provided feedback to decrease the pressure on the activity tracking device. As shown in FIG. 7C the decrease pressure feedback can be in the form of one or more arrows pointing up or away from the user's finger. Alternatively, the activity device can flash a portion or all of the display 122 or display icons or words such as "lighten up" or vibrate or other suitable tactile feedback, visual feedback, or audible feedback to the user.

The detected heart beats are constantly monitored for usability, in an operation 730. If decreasing the pressure provides usable heart beat data then the method operations return to operation 525 in FIG. 5. If decreasing the pressure does not provide usable heart beat data then the method operations continue in operation 715 as described above.

Figure 8:
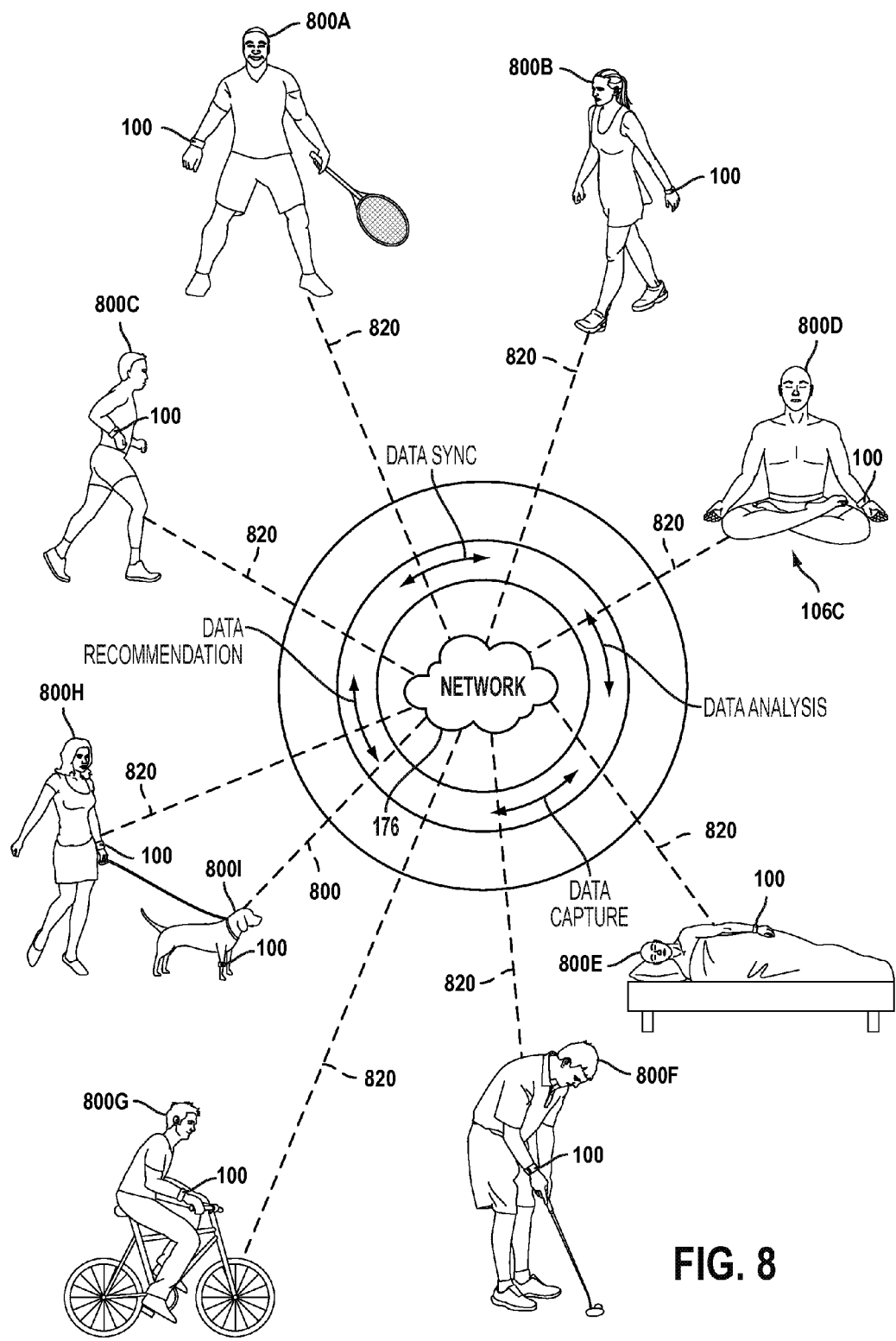
FIG. 8 illustrates an example where various types of activities of users can be captured by activity tracking devices, in accordance with embodiments of the present invention.

FIG. 8 illustrates an example where various types of activities of users 800A-800I can be captured by activity tracking devices 100, in accordance with embodiments of the present invention. As shown, the various types of activities can generate different types of data that can be captured by the activity tracking device 100. The data, which can be represented as motion data (or processed motion data) can be transferred 820 to a network 176 for processing and saving by a server, as described above. In one embodiment, the activity tracking device 100 can communicate to a device using a wireless connection, and the device is capable of communicating and synchronizing the captured data with an application running on the server. In one embodiment, an application running on a local device, such as a smart phone or tablet or smart watch can capture or receive data from the activity tracking device 100 and represent the tract motion data in a number of metrics.

In one embodiment, the device collects one or more types of physiological and/or environmental data from embedded sensors and/or external devices and communicates or relays such metric information to other devices, including devices capable of serving as Internet-accessible data sources, thus permitting the collected data to be viewed, for example, using a web browser or network-based application. For example, while the user is wearing an activity tracking device, the device may calculate and store the user's step count using one or more sensors. The device then transmits data representative of the user's step count to an account on a web service, computer, mobile phone, or health station where the data may be stored, processed, and visualized by the user. Indeed, the device may measure or calculate a plurality of other physiological metrics in addition to, or in place of, the user's step count.

Some physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Still further, other metrics can include, without limitation, calories burned by a user, weight gained by a user, weight lost by a user, stairs ascended, e.g., climbed, etc., by a user, stairs descended by a user, variation in the user's altitude, steps taken by a user during walking or running, a number of rotations of a bicycle pedal rotated by a user, sedentary activity data, driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active. In some embodiments, a user may stand on a monitoring device that determines a physiological parameter of the user. For example, a user stands on a scale that measures a weight, a body fat percentage, a biomass index, or a combination thereof, of the user.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive.

This information can be associated to the users account, which can be managed by an activity management application on the server. The activity management application can provide access to the users account and data saved thereon. The activity manager application running on the server can be in the form of a web application. The web application can provide access to a number of websites screens and pages that illustrate information regarding the metrics in various formats. This information can be viewed by the user, and synchronized with a computing device of the user, such as a smart phone.

In one embodiment, the data captured by the activity tracking device 100 is received by the computing device, and the data is synchronized with the activity measured application on the server. In this example, data viewable on the computing device (e.g. smart phone) using an activity tracking application (app) can be synchronized with the data present on the server, and associated with the user's account. In this way, information entered into the activity tracking application on the computing device can be synchronized with application illustrated in the various screens of the activity management application provided by the server on the website.

The user can therefore access the data associated with the user account using any device having access to the Internet. Data received by the network 176 can then be synchronized with the user's various devices, and analytics on the server can provide data analysis to provide recommendations for additional activity, and or improvements in physical health. The process therefore continues where data is captured, analyzed, synchronized, and recommendations are produced. In some embodiments, the captured data can be itemized and partitioned based on the type of activity being performed, and such information can be provided to the user on the website via graphical user interfaces, or by way of the application executed on the users smart phone (by way of graphical user interfaces).

In an embodiment, the sensor or sensors of a device 100 can determine or capture data to determine an amount of movement of the monitoring device over a period of time. The sensors can include, for example, an accelerometer, a magnetometer, a gyroscope, or combinations thereof. Broadly speaking, these sensors are inertial sensors, which capture some movement data, in response to the device 100 being moved. The amount of movement (e.g., motion sensed) may occur when the user is performing an activity of climbing stairs over the time period, walking, running, etc. The monitoring device may be worn on a wrist, carried by a user, worn on clothing (using a clip, or placed in a pocket), attached to a leg or foot, attached to the user's chest, waist, or integrated in an article of clothing such as a shirt, hat, pants, blouse, glasses, and the like. These examples are not limiting to all the possible ways the sensors of the device can be associated with a user or thing being monitored.

In other embodiments, a biological sensor can determine any number of physiological characteristics of a user. As another example, the biological sensor may determine heart rate, a hydration level, body fat, bone density, fingerprint data, sweat rate, and/or a bioimpedance of the user. Examples of the biological sensors include, without limitation, a biometric sensor, a physiological parameter sensor, a pedometer, or a combination thereof.

In some embodiments, data associated with the user's activity can be monitored by the applications on the server and the users device, and activity associated with the user's friends, acquaintances, or social network peers can also be shared, based on the user's authorization. This provides for the ability for friends to compete regarding their fitness, achieve goals, receive badges for achieving goals, get reminders for achieving such goals, rewards or discounts for achieving certain goals, etc.

In some embodiments the heart beats are detected by processing the light received in the light detector, within the sampling time period. A first time interval between a first beat of the detected heart beats and a second heart beat is measured. The sample time interval can be divided by the first time interval to determine a first estimate of heart beats detected within the sampling time period and the first estimate of heart beats within the sampling time period can be extrapolated to a first estimated heart beats per minute. The first estimate heart beats per minute can be output to the display screen. At least one beat can be added to the first estimate of heart beats to produce a second estimate of heart beats that can be scored with the first estimate of heart beats. A highest scoring of the first estimate of heart beats and the second estimate of heart beats can be selected and output to the display screen.

In another embodiment, at least one beat can be subtracted from the first estimate of beats to produce a third estimate of heart beats. The first estimate of heart beats and the third estimate of heart beats can be scored. A highest scoring of the first estimate of heart beats and the third estimate of heart beats can be selected and output to the display screen.

In another embodiment, identifying the heart beats of the user and producing an indication of a heart rate can include identifying and filtering a falsely detected heart beat coinciding with motion detected by the motion sensor. By way of example, a user's motion may be erroneously identified as a heart beat. The processor can compare detected motion (i.e., motion data, instantaneous shocks, etc.) to the detected heart beats and identify heart beats that coincide with motion data. Further, as the motion data and heart beat data are compiled over time, detected motions that often produce corresponding erroneously detected heart beats can be identified and filtered from the detected heart beats.

In another embodiment, activity tracking device includes a housing including a motion sensor and a processor. The processor is configured for processing motion data produced by the motion sensor. A display screen is integrated with the housing to display metrics that quantify the motion data produced by the motion sensor. A light source is integrated within the housing to enable light to be directed out of the housing at a heart rate monitor location on the housing. A light detector is also integrated within the housing. The light detector is configured to capture an amount of the light that is reflected back to the light detector, at least a first portion of the light reflected back to the light detector is reflected from a blood vessel disposed under a skin of a user when the user places the skin over the heart rate monitor location on the housing. The processor can be in communication with the light detector to enable processing of the reflected light to identify heart beats of the user and produce an indication of a heart rate. The indication of the heart rate being displayable on the display screen as an option, in addition to the metrics that quantify the motion data. The heart rate can be calculated based on an algorithm that calculates a first estimate of heart beats per minute corresponding to detected heart beats in the light received in the light detector within a sampling time period. A refined estimate of heart beats per minute can be calculated by adding at least one beat to the first estimate of heart beats to produce a second estimate of heart beats and subtracting at least one beat from the first estimate of beats to produce a third estimate of heart beats. The first estimate of heart beats, the second estimate of heart beats and the third estimate of heart beats are scored and a highest scoring estimate of heart beats is selected and output to the display screen.

As noted, an activity tracking device 100 can communicate with a computing device (e.g., a smartphone, a tablet computer, a desktop computer, or computer device having wireless communication access and/or access to the Internet). The computing device, in turn, can communicate over a network, such as the Internet or an Intranet to provide data synchronization. The network may be a wide area network, a local area network, or a combination thereof. The network may be coupled to one or more servers, one or more virtual machines, or a combination thereof. A server, a virtual machine, a controller of a monitoring device, or a controller of a computing device is sometimes referred to herein as a computing resource. Examples of a controller include a processor and a memory device.

In one embodiment, the processor may be a general purpose processor. In another embodiment, the processor can be a customized processor configured to run specific algorithms or operations. Such processors can include digital signal processors (DSPs), which are designed to execute or interact with specific chips, signals, wires, and perform certain algorithms, processes, state diagrams, feedback, detection, execution, or the like. In some embodiments, a processor can include or be interfaced with an application specific integrated circuit (ASIC), a programmable logic device (PLD), a central processing unit (CPU), or a combination thereof, etc.

In some embodiments, one or more chips, modules, devices, or logic can be defined to execute instructions or logic, which collectively can be viewed or characterized to be a processor. Therefore, it should be understood that a processor does not necessarily have to be one single chip or module, but can be defined from a collection of electronic or connecting components, logic, firmware, code, and combinations thereof.

Examples of a memory device include a random access memory (RAM) and a read-only memory (ROM). A memory device may be a Flash memory, a redundant array of disks (RAID), a hard disk, or a combination thereof.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relate to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure are not to be limited to the details given herein, but may be modified within the scope and equivalents of the appended claims.

What is claimed is:
1. An activity tracking device, comprising,
a housing, the housing including:
a motion sensor and a processor, the processor configured for processing motion data produced by the motion sensor;
a display screen integrated with the housing to display metrics that quantify the motion data produced by the motion sensor;
a light source integrated within the housing to enable light to be directed out of the housing at a heart rate monitor location on the housing; and a light detector integrated within the housing, the light detector configured to capture an amount of the light that is reflected back to the light detector, at least a first portion of the light reflected back to the light detector is reflected from a blood vessel under a skin of a user when the user places the skin over the heart rate monitor location on the housing, the processor further being in communication with the light detector to enable processing of the reflected light, the processing configured to identify heart beats of the user and produce an indication of a heart rate, the indication of the heart rate being displayable on the display screen as an option, in addition to the metrics that quantify the motion data, the processor including computer executable instructions for measuring a baseline reflectance signal of the light reflected from the blood vessel between each one of a plurality of heart beats and for detecting a second reflectance signal corresponding to at least one heart beat in the blood vessel, the second reflectance signal being less than the baseline reflectance signal, where the blood vessel scatters more of the light during the at least one heart beat than between each one of the plurality of heart beats, wherein the heart rate monitor location includes a button and the button has an infrared (IR) light transmitting structure, the light source and the light detector are disposed substantially below the button.

2. The activity tracking device of claim 1, wherein the motion sensor is one of or includes an accelerometer, or a global positioning sensor, or a magnetometer, or a gyroscope, or a rotary encoder, or a calorie measurement sensor, or a moisture measurement sensor, or a displacement sensor, or an ultrasonic sensor, or a pedometer, or an altimeter, or a linear motion sensor, or an angular motion sensor, or a multi-axis motion sensor, or a combination of two or more thereof.

3. The activity tracking device of claim 1, further comprising:
a communication transceiver configured for communicating via at least one a wireless network;
an ambient light sensor; and
an indicator for visually identifying the heart rate monitor location on the housing.

4. The activity tracking device of claim 1, further comprising, at least one infrared (IR) proximity sensor associated with the light source and light detector, the IR proximity sensor configured to activate the light source and light detector upon detecting presence of the skin of the user, wherein detecting presence of the skin of the user further functions to navigate to one or more metrics of the display screen.

5. The activity tracking device of claim 1, further comprising,
a pressure detecting system configured for detecting a pressure applied to the heart rate monitor location on the housing with the skin of the user during the identification of heart beats; and
the activity tracking device outputs at least one a feedback signal regarding the detected pressure applied to the heart rate monitor location, the feedback indication being indicative of more or less pressure desired to produce the heart rate, the feedback signal including at least one of a visual signal, a graphic signal, a tactile signal, and an audible signal.

6. The activity tracking device of claim 5, wherein the pressure detecting system includes at least one of a group consisting of:

processing of the reflected light, the processing configured to identify one of an excess pressure, an insufficient pressure or an acceptable pressure from the detected heart beats of the user; or
a pressure sensor disposed near light source and the light detector.

7. The activity tracking device of claim 1, further comprising, the display screen including one or both of waveform data or numerical data when the skin of the user is over the heart rate monitor location and the heart beats are being identified over a sampling time period; and
upon concluding the sampling time period, displaying the heart rate on the display screen.

8. The activity tracking device of claim 7, further comprising, at least one recalled heart rate displayed on the display screen.

9. The activity tracking device of claim 1, wherein the light detector is disposed next to the light source.

10. An activity tracking device, comprising:
a housing, the housing including:
a motion sensor and a processor, the processor configured for processing motion data produced by the motion sensor;
a display screen integrated with the housing to display metrics that quantify the motion data produced by the motion sensor;
a light source integrated within the housing to enable light to be directed out of the housing at a heart rate monitor location on the housing; and
a light detector integrated within the housing, the light detector configured to capture an amount of the light that is reflected back to the light detector, at least a first portion of the light reflected back to the light detector is reflected from a blood vessel under a skin of a user when the user places the skin over the heart rate monitor location on the housing, the processor further being in communication with the light detector to enable processing of the reflected light, the processing configured to identify heart beats of the user and produce an indication of a heart rate, the indication of the heart rate being displayable on the display screen as an option, in addition to the metrics that quantify the motion data, the processor including computer executable instructions for measuring a baseline reflectance signal of the light reflected from the blood vessel between each one of a plurality of heart beats and for detecting a second reflectance signal corresponding to at least one heart beat in the blood vessel, the second reflectance signal being less than the baseline reflectance signal, where the blood vessel scatters more of the light during the at least one heart beat than between each one of the plurality of heart beats, wherein the heart rate is calculated based on an algorithm that:
detects the plurality of heart beats in the light received in the light detector within a sampling time period;
measures a first time interval between a first beat of the detected plurality of heart beats and a second beat of the detected plurality of heart beats;
divides the sample time interval by the first time interval to determine a first estimate of heart beats detected within the sampling time period;
extrapolates the first estimate of heart beats within the sampling time period to a first estimated heart beats per minute;
outputs the first estimate heart beats per minute to the display screen adds at least one beat to the first estimate of heart beats to produce a second estimate of heart beats;

subtracts at least one beat from the first estimate of beats to produce a third estimate of heart beats;

scores the first estimate of heart beats, the second estimate of heart beats and the third estimate of heart beats;

selects a highest scoring of the first estimate of heart beats, the second estimate of heart beats and the third estimate of heart beats; and outputs the selected estimated heart beats per minute to the display screen.

11. The activity tracking device of claim 1, further comprising, two proximity sensors at least one of the two proximity sensors including the light source and light detector.

12. The activity tracking device of claim 1, wherein the light source and the reflected light detector can be selected for any suitable wavelength or suitable band of wavelengths of light ranging from between infrared wavelengths through a human visible spectrum to ultraviolet wavelengths.

13. The activity tracking device of claim 1, wherein the light source includes at least one of:

an infrared (IR) light source, wherein the IR light emitted from the light source produces a deadfront at the heart rate monitor location of the housing; or a green light source and the heart rate monitor location includes a translucent green window.

14. The activity tracking device of claim 1, wherein the heart rate monitor location includes a cover that enables infrared (IR) light of the light source to pass while blocking substantially all light in a human visible spectrum.

15. The activity tracking device of claim 1, wherein the light source and light detector additionally function as a proximity sensor to activate the display screen.

16. The activity tracking device of claim 1, wherein the button further functions to navigate to one or more metrics of the display screen and, wherein the functions to navigate are enabled while the heart beats are measured.

17. The activity tracking device of claim 1, wherein the skin is of a finger of a user.

18. The activity tracking device of claim 1, wherein the button includes a pressure sensor configured for detecting a pressure applied to the button, the pressure sensor consisting of at least one of a strain gauge, a push resistance, or a force sensitive film.

19. The activity tracking device of claim 1, wherein the processing configured to identify heart beats of the user can also include processing for determining a stress level of the user corresponding to at least one of a detected heart rate or a heart rate variation as compared to previously determined heart rate.

20. The activity tracking device of claim 1, wherein the processing configured to identify heart beats of the user can also include processing for determining a number of stairs the user has ascended and/or descended and/or determining a user's change in altitude.

21. The activity tracking device of claim 1, the processing configured to identify heart beats of the user can also include processing for determining active minutes of the user.

22. The activity tracking device of claim 1, further comprising at least one marking on the housing to identify a location of the heart rate monitor on the housing.

* * * * *